(12) United States Patent
Blainey et al.

(10) Patent No.: US 12,054,764 B2
(45) Date of Patent: Aug. 6, 2024

(54) HIGH-THROUGHPUT SCREENS FOR EXPLORING BIOLOGICAL FUNCTIONS OF MICROSCALE BIOLOGICAL SYSTEMS

(71) Applicants: THE BROAD INSTITUTE, INC., Cambridge, MA (US); MASSACHUSETTS INSTITUTE OF TECHNOLOGY, Cambridge, MA (US)

(72) Inventors: Paul Blainey, Cambridge, MA (US); Navpreet Ranu, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 448 days.

(21) Appl. No.: 16/605,156

(22) PCT Filed: Apr. 13, 2018

(86) PCT No.: PCT/US2018/027631
§ 371 (c)(1),
(2) Date: Oct. 14, 2019

(87) PCT Pub. No.: WO2018/191701
PCT Pub. Date: Oct. 18, 2018

(65) Prior Publication Data
US 2021/0139941 A1    May 13, 2021

Related U.S. Application Data

(60) Provisional application No. 62/485,529, filed on Apr. 14, 2017.

(51) Int. Cl.
*C12Q 1/04*   (2006.01)
*C12N 11/04*  (2006.01)
*C12N 15/10*  (2006.01)
*C12Q 1/18*   (2006.01)
*C12Q 1/6858* (2018.01)

(52) U.S. Cl.
CPC ............ *C12Q 1/04* (2013.01); *C12N 11/04* (2013.01); *C12N 15/1075* (2013.01); *C12N 15/1086* (2013.01); *C12Q 1/18* (2013.01); *C12Q 1/6858* (2013.01); *C12Q 2563/159* (2013.01); *C12Q 2565/629* (2013.01)

(58) Field of Classification Search
CPC ... C12N 11/04; C12N 15/10; C12Q 2563/159
See application file for complete search history.

(56) References Cited

U.S. PATENT DOCUMENTS

2005/0070005 A1    3/2005  Keller
2010/0311107 A1*  12/2010  Baltz ............... C12N 1/20
                                            435/32
2012/0270295 A1   10/2012  Choo et al.
2013/0203605 A1*   8/2013  Shendure ........... C12N 15/1093
                                            506/2
2015/0376609 A1*  12/2015  Hindson .............. C40B 50/16
                                            506/4

FOREIGN PATENT DOCUMENTS

| WO | 2012156744 A2 | 11/2012 | |
| WO | WO-2012156744 A2 * | 11/2012 | ......... C12N 15/1075 |
| WO | 2014047561 A1 | 3/2014 | |
| WO | WO-2014124336 A2 * | 8/2014 | ......... C12N 15/1065 |
| WO | WO-2015069798 A1 * | 5/2015 | ........... C12Q 1/6858 |
| WO | 2016040476 A1 | 3/2016 | |
| WO | 2016089920 A1 | 6/2016 | |
| WO | 2016126871 A2 | 8/2016 | |
| WO | 2016145416 A2 | 9/2016 | |

(Continued)

OTHER PUBLICATIONS

Eun et al. ("Encapsulating bacteria in agarose microparticles using microfluidics for high-throughput cell analysis and isolation." ACS chemical biology 6.3 (2011): 260-266 ). (Year: 2011).*
Eun et al. (2011): supplementary information. (Year: 2011).*
Zhang, Xulang, et al. "A biodegradable, immunoprotective, dual nanoporous capsule for cell-based therapies." Biomaterials 29.31 (2008): 4253-4259. (Year: 2008).*
"International Preliminary Report on Patentability issued in International Patent Application No. PCT/US2018/027631 filed Apr. 13, 2018", mailed Oct. 24, 2019, 14 pages.
Blasi, et al., "Label-free cell cycle analysis for high-throughput imaging flow cytometry", Nature Communications 2016, DOI:10.1038/ncomms10256, 9 pages.

(Continued)

*Primary Examiner* — Sahana S Kaup
(74) *Attorney, Agent, or Firm* — F. Brent Nix, Esq.; Johnson, Marcou, Isaacs & Nix, LLC

(57) ABSTRACT

Provided herein are methods for screening biological functions of microscale biological systems comprises segregating each microscale biological system from a set of microscale biological systems to be screened into individual discrete volumes, the individual discrete volume comprising a first polymer. The first polymer is then forced or allowed to polymerize to form a set of polymerized beads that encapsulate an individual microscale biological system. The polymerized beads are further encapsulated in a second droplet comprising a second polymer and one or more reporter elements. The reporter elements are configured to produce a readout upon detecting the absence or presence of a biological function to be screened. The second polymer is then forced or allowed to polymerize to form an outer capsule around each individual bead thereby forming a set of encapsulated beads. One or more biological functions of the double-encapsulated system are identified by detecting the readout of the reporters.

30 Claims, 37 Drawing Sheets

(56) References Cited

FOREIGN PATENT DOCUMENTS

WO    WO-2016145416 A2 *   9/2016   .........  C12N 15/1075

OTHER PUBLICATIONS

Eun, et al., "Encapsulating bacteria in agarose microparticles using microfluidics for high-throughput cell analysis and solation", ACS Chem Biol. Mar. 18, 2011, Mar. 18, 2011, 34 pages.

Klein, et al., "Droplet Barcoding for Single-Cell Transcriptomics Applied to Embryonic Stem Cells", Cell, vol. 161, No. 5, May 21, 2015, 24 pages.

Mascosko, et al., "Highly Parallel Genome-wide Expression Profiling of Individual Cells Using Nanoliter Droplets", Cell, 2015, 161:1202-1214, 14 pages.

Thomas, "International Search Report and Written Opinion of PCT/US2018/027631", mailed Jul. 2, 2018, 32 pages.

* cited by examiner

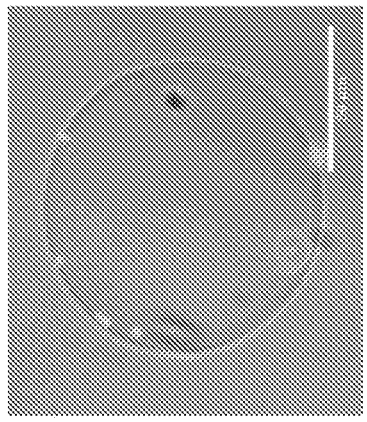
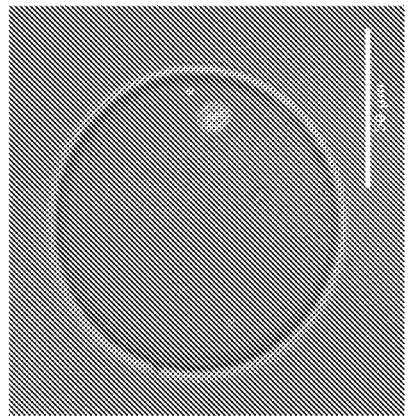
FIG. 33A
FIG. 33D
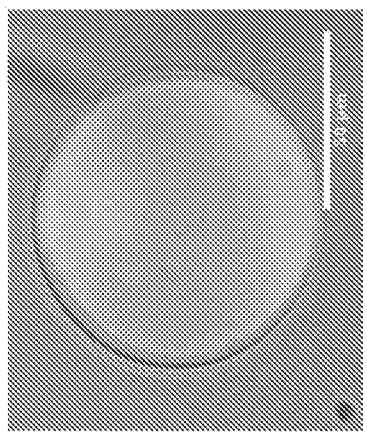
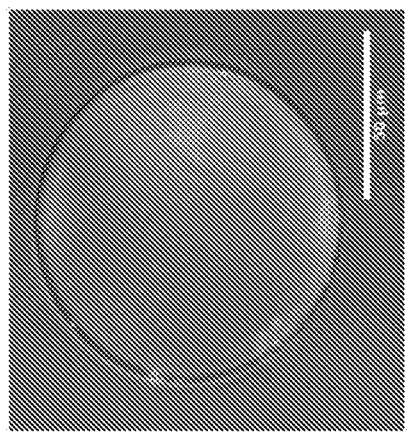
FIG. 33B
FIG. 33E
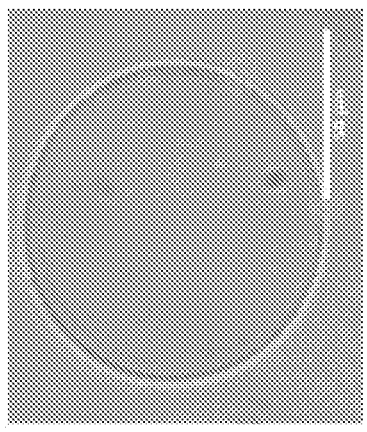
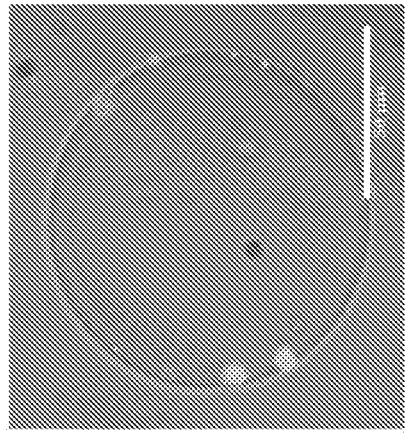
FIG. 33C
FIG. 33F

HIGH-THROUGHPUT SCREENS FOR EXPLORING BIOLOGICAL FUNCTIONS OF MICROSCALE BIOLOGICAL SYSTEMS

CROSS-REFERENCE TO RELATED APPLICATIONS

This application is a 35 U.S.C. § 371 national stage application of International Patent Application No. PCT/US2018/027631 filed Apr. 13, 2018, and entitled "High-Throughput Screens for Exploring Biological Functions of Microscale Biological Systems," and claims the benefit of U.S. Provisional Application No. 62/485,529, filed Apr. 14, 2017. The entire contents of the above-identified applications are hereby fully incorporated herein by reference.

TECHNICAL FIELD

The subject matter disclosed herein is generally directed to methods, devices, and reagents for high-throughput biological function screens for cellular and acellular samples.

BACKGROUND

Natural products are an important class of molecules due to their functions as antimicrobials, antifungals, immunosuppressants, and antitumor agents. However, their discovery remains a challenging problem. Progress has been made in identifying the capacity of microorganisms to produce these compounds, but the reality is that many environmental bacteria are difficult to work with under laboratory conditions. Since their introduction in therapy, antibiotics have played an essential role in human society, saving millions of lives, allowing safe surgery, organ transplants, and cancer therapy.

Antibiotics are, for the vast majority, low molecular weight (<1000 Da) secondary products of microbial, fungal or plant metabolism. Several lines of evidence suggest that these or similar molecules may have been around since the pre-biotic era and may have played an important role as modulators or effectors of the primeval RNA molecules from which "modern" biological structures like the ribosomes and riboswitches have evolved. Indeed, the fact that several antibiotics may have coevolved with RNA is suggested by the fact that they bind select RNA targets and that some of them, like the aminoglycosides, can equally influence ribosomal decoding and inhibit the second step of Group I T4 phage-derived td intron splicing, two activities possibly having a common origin in the "RNA World."

Since their discovery and their first therapeutic applications, antibiotics can be credited with having saved millions of human lives. Nevertheless, after an initial period in which the detection, biological, pharmacological and clinical characterization as well as marketing of new antibiotics have flourished, the discovery of new anti-infective agents has slowed down considerably. This has resulted in a long "innovation gap" which extends from 1962, when quinolones and streptogramin were first applied in human therapy, until 2000, when oxazolinidones were introduced.

SUMMARY

In one example embodiment, a method for screening biological functions of microscale biological systems comprises segregating each microscale biological system from a set of microscale biological systems to be screened into individual discrete volumes, the individual discrete volume comprising a first polymer. The first polymer is then forced or allowed to polymerize, depending on the polymer used, to form a set of polymerized beads that encapsulate an individual microscale biological system. The polymerized beads are then further encapsulated in a second droplet comprising a second polymer and one or more reporter elements. The reporter elements are configured to produce a readout upon detecting the absence or presence of a biological function to be screened. The second polymer is then forced or allowed to polymerize to form an outer capsule around each individual bead thereby forming a set of encapsulated beads. One or more biological functions of the double-encapsulated microscale biological system are then identified by detecting the readout of the one or more reporter elements.

The microscale biological systems comprise naturally occurring cells. The naturally occurring cells may be prokaryotic, eukaryotic, or a mixture thereof. The naturally occurring cells may be derived from clinical isolates or environmental samples. In certain example embodiments, the naturally occurring cells may be prokaryotic cells to be screened for antibiotic production. In certain other example embodiments, the microscale biological system may comprise engineered cells. The engineered cells may comprise one or more genetic perturbations. In certain example embodiments, the microscale biological systems may comprise cell free systems. The cell free systems may comprise one or more nucleic acid constructs encoding one or more gene expression products or gene expression regulator elements.

The polymer used to form the bead and outer capsule may be the same or different. In certain example embodiments the polymer used to form the bead, the outer capsule, or both is a hydrogel polymer. The hydrogel polymer may comprise a polysaccharide, a synthetic polymer, a natural polymer, and/or a block copolymer. The polysaccharide may comprise hydroxyethyl cellulose.

In certain example embodiments, the method may further comprise sorting the encapsulated gel beads based at least in part on the detected readout of the one or more reporter elements, isolating the sorted encapsulated beads identified as having one or more target biological functions. In certain example embodiments, one or more chemical or biological agents produced by the microscale biological system may be isolated and analyzed to determine one of more properties of said chemical or biological agents. The chemical or biological agents may be an expressed RNA, a protein, a lipid, a polysaccharide, a small molecule, a metabolite, or a combination thereof. In certain example embodiments, the method may further comprise introducing one or more capture agents for the one or more chemical or biological agents into the bead, outer capsule, or both to facilitate isolation of the chemical or biological agent.

In certain example embodiments, the method may further comprise sequencing the microscale biological systems. In order to identify the sequence of a microscale biological system as originating from a particular bead, the microscale biological system, or its transcripts, may be labeled with an origin-specific barcode prior to sequencing. In the context of cell free microscale biological systems comprising one or more nucleic acid constructs, sequencing may comprise sequencing of the one or more nucleic acid constructs. In the context of a cellular microscale biological system, sequencing may comprise sequencing a genome of the cell, RNA transcripts of the cell, or an entire transcriptome of the cell.

In certain example embodiments, determining a genotype for each cell comprises lysing the cell in each bead such that genomic DNA is retained in the polymerized bead, releasing the beads from the outer capsule and re-encapsulating the beads in a second outer capsule, the second outer capsule comprising genomic DNA amplification reagents. The beads are maintained under conditions sufficient for genomic DNA amplification. The beads are then released from the second capsule and re-encapsulated in a third capsule comprising tagmentation reagents to generate genomic fragments, the tagmentation reagents comprising transposomes loaded with sequencing adapters. The sequencing adapters may further comprise a unique origin specific barcode or unique combination of origin specific barcodes. After maintaining the encapsulated beads under conditions sufficient for tagmentation, the tagmented DNA is then isolated to prepare a DNA sequencing library comprising the genomic DNA fragments. The genomic DNA library is then sequenced to determine a genotype for each microscale biological system. In certain example embodiments, the DNA amplification reagents are multiple displacement amplification reagents (MDA). In certain example embodiments, the method may further comprise a DNA sequencing library amplification step prior to the sequencing step. In certain example embodiments, the DNA sequencing library amplification step comprises releasing each encapsulated bead into a separate individual discrete volume comprising DNA amplification reagent, breaking the bead to release the genomic DNA fragments labeled with sequencing adapters, and optionally origin-specific barcodes, and maintaining the separate individual discrete volumes under conditions sufficient to allow for DNA amplification. In certain example embodiments, the amplification step may further comprise addition of a second barcode to each genomic DNA fragment.

In certain example embodiments, the contents of the bead, the outer capsule, or both may be altered over the time-course of a given assay. In certain example embodiments, the contents are altered by contacting the double encapsulated microscale biological system with one or more reagents that are diffusible into the outer shell and/or bead. The one or more reagents may be used to sustain replication or growth of the microscale biological system, or determine an additional biological function of the microscale biological system. In certain other example embodiments, altering the contents may comprise releasing the beads from the first outer capsule and re-encapsulating the beads in an additional outer capsule. The process of releasing and re-encapsulating the beads to introduce additional agents may be repeated over multiple iterations as needed per assay design. In addition, the beads may be sorted, for example, based on the readout of a reporter element, between each iteration of release and re-encapsulation. In some embodiments, a reporter element described herein may produce an optically detectable signal. In one embodiment, the reporter element comprises magnetic-based separation, and may comprise labeling a biological molecule of interest with a magnetic particle and isolating the biological molecule of interest using the magnetic particles. In another embodiment, the biological molecule of interest is selected from the group consisting of a protein, a cell surface marker, and a nucleic acid, or combinations thereof.

In certain example embodiments the reporter element is a reporter cell and the readout comprises cell growth, cell death, changes in reporter cell gene expression, changes in reporter cell epigenetic modifications or chromatin structure, or changes in cell phenotype. In certain example embodiments, the readout may be expression of a detectable gene expression product, such as an mRNA or protein. In certain example embodiments, the detectable gene expression product is operatively coupled to a promoter that is inhibited or induced by one or more biological functions of the microscale biological system. In certain embodiments, the promoter may be a stress promoter. In certain example embodiments, the detectable gene expression product is a fluorescent protein.

These and other aspects, objects, features, and advantages of the example embodiments will become apparent to those having ordinary skill in the art upon consideration of the following detailed description of illustrated example embodiments.

An empty bead droplet. (Middle) Brightfield image of *S. niveus* showing filament protrusion out into the aqueous phase. (Right) DNA stained with propidium iodide (PI) following lysis and washing within an agarose droplet. Genomic DNA is too large to diffuse out through the pore of agarose. The filaments are also visible which are crucial to *Streptomyces* life cycle and antibiotic production. The bottom panel shows the *S. niveus* life cycle.

Figure 7:
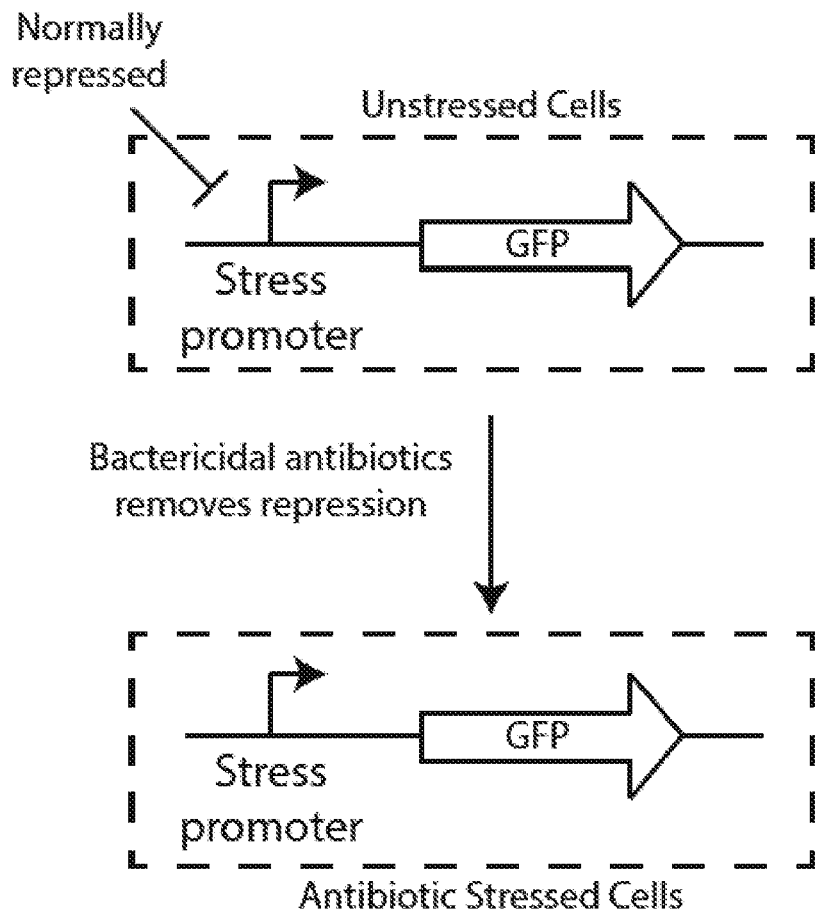

FIG. 7 shows a schematic showing an example reporter element for measuring a biological function of a microscale biological system via a SOS response element placed upstream of a fluorescent protein.

Figure 8:
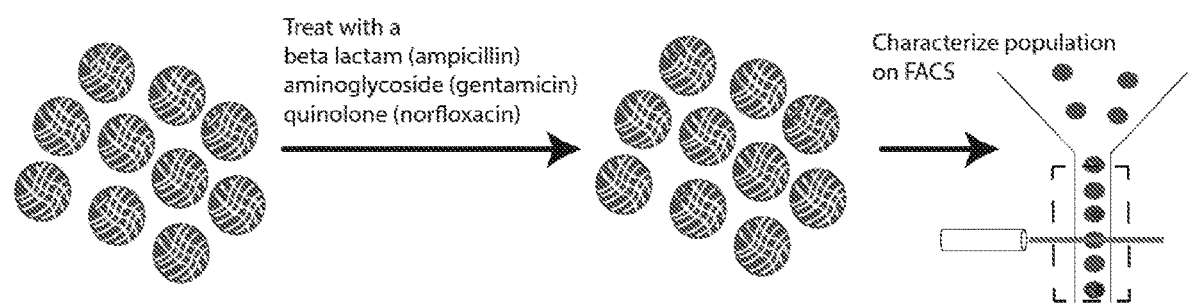

FIG. 8 shows a schematic showing an example method for separating encapsulated microscale biological systems on the basis of a reporter element readout.

Figure 9:
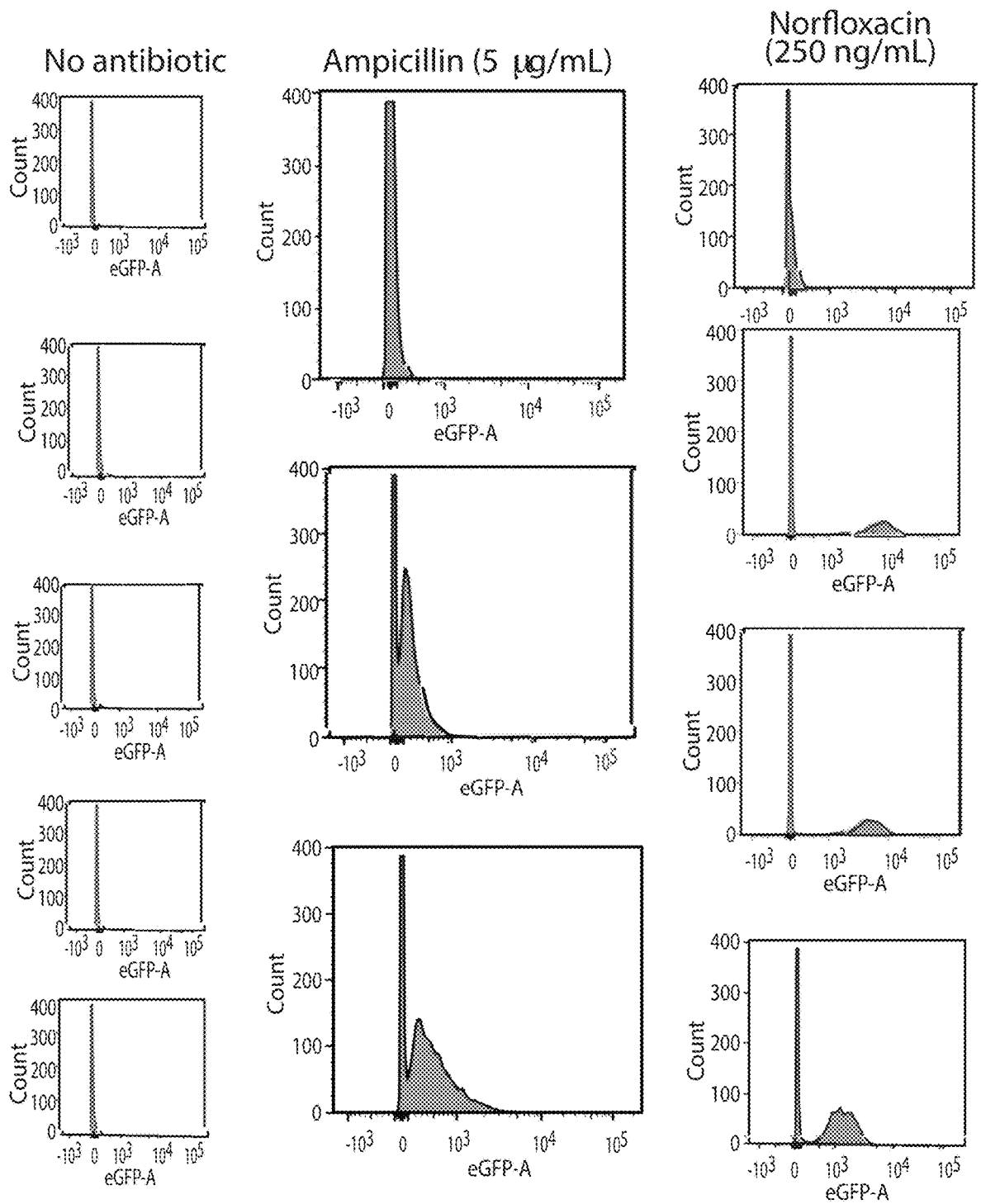

FIG. 9 shows a set of histograms showing antibiotic induced fluorescence from reporter elements comprising stress reporters.

Figure 10:
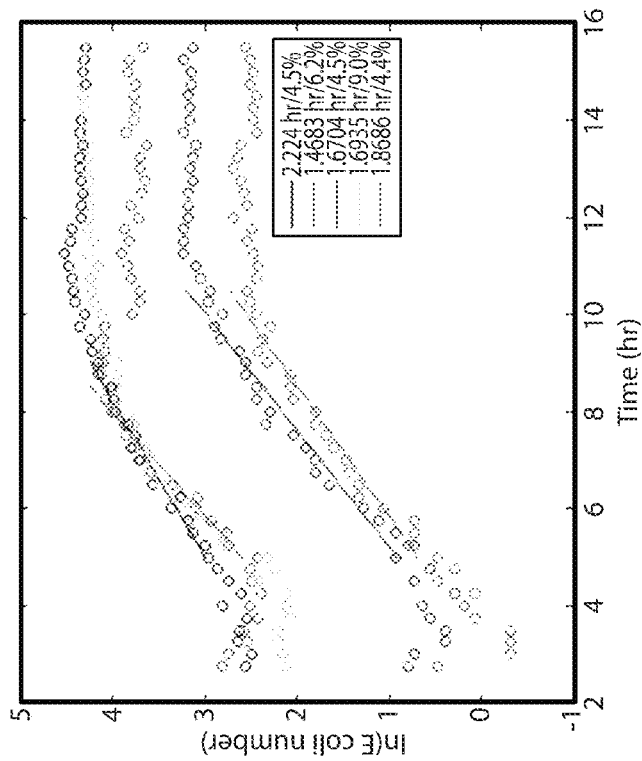
Figure 10:
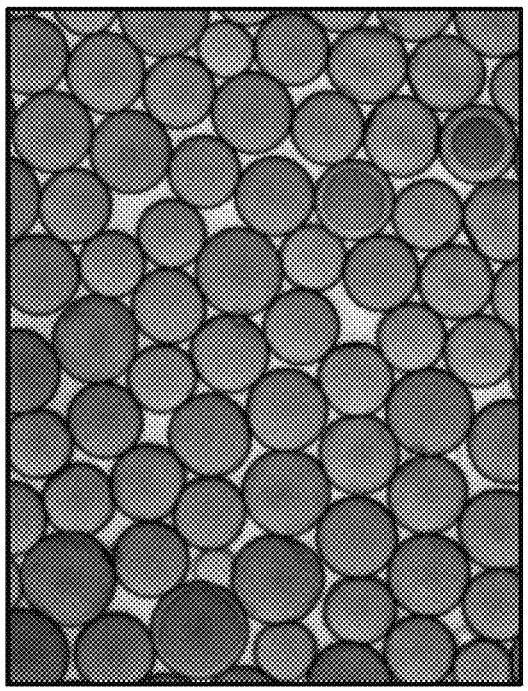
Figure 10:
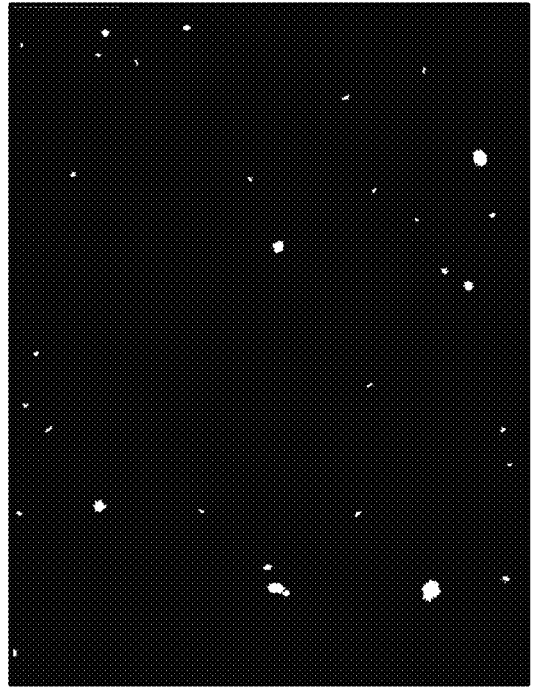

FIG. 10. shows a set of figures showing the dynamics of fluorescent stress response signal in 2% ultra-low melt agarose droplets. Ampicillin was loaded at 5 μg/mL, at the minimum inhibitory concentration (MIC) for *E. coli*. A bimodal distribution is seen (objects with similar size, but different fluorescence levels).

Figure 11:
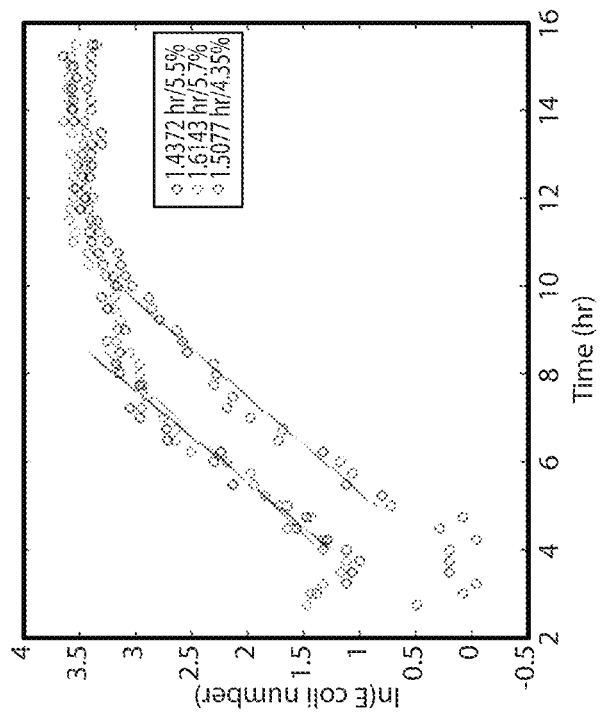
Figure 11:
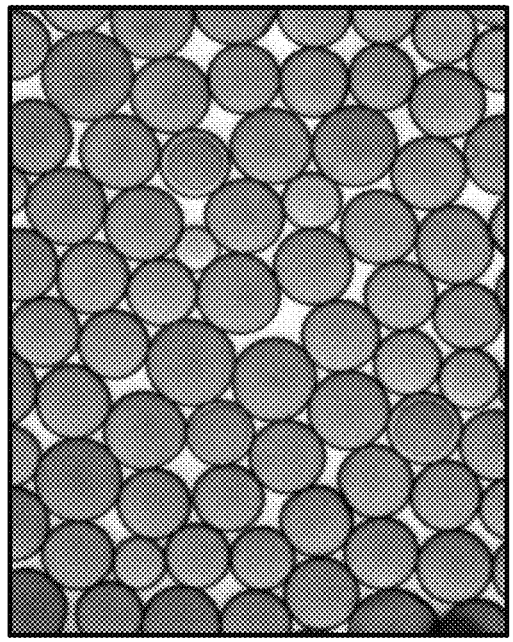
Figure 11:
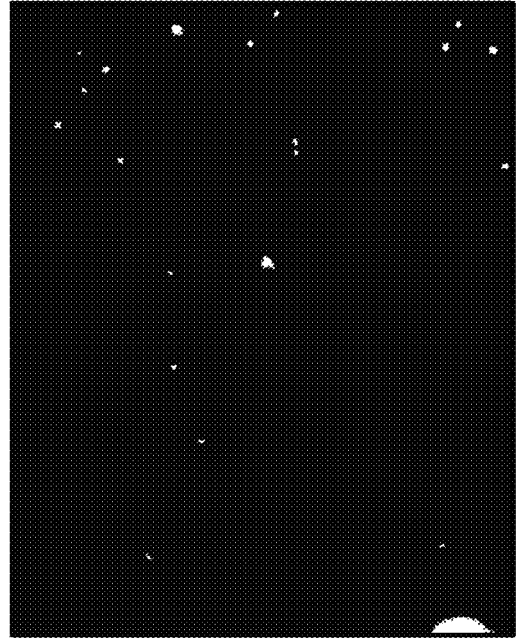

FIG. 11 shows a set of figures showing the measurement of colony size to estimate *E. coli* concentration. Max intensity projection of initial fluorescent images. The images are converted to binary, and spherical colony growth is assumed to extract radius of fluorescent colonies. The number of cells is estimated by dividing volume of sphere with *E. coli* volume (1.1 um$^3$).

Figure 12:
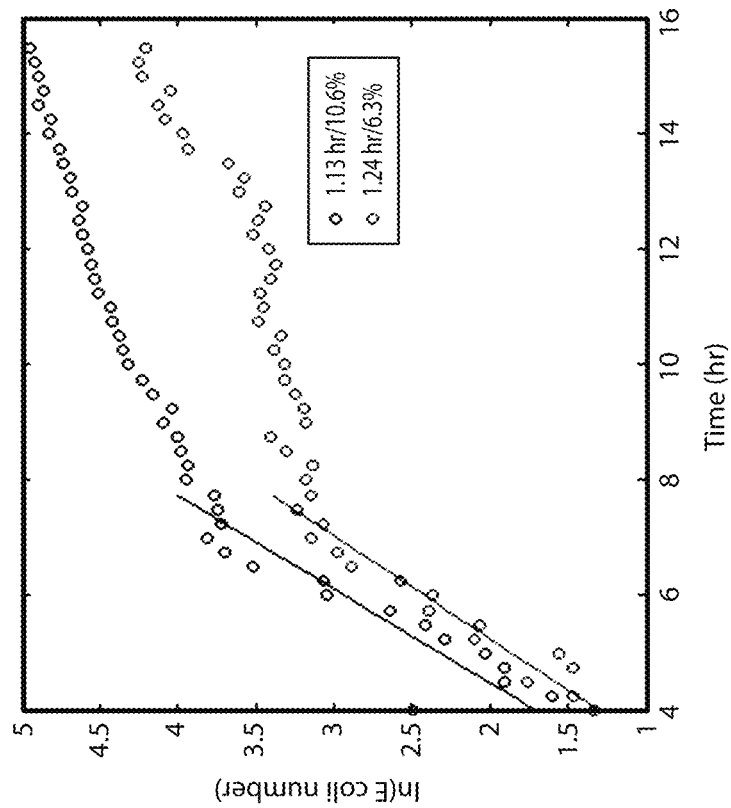
Figure 12:
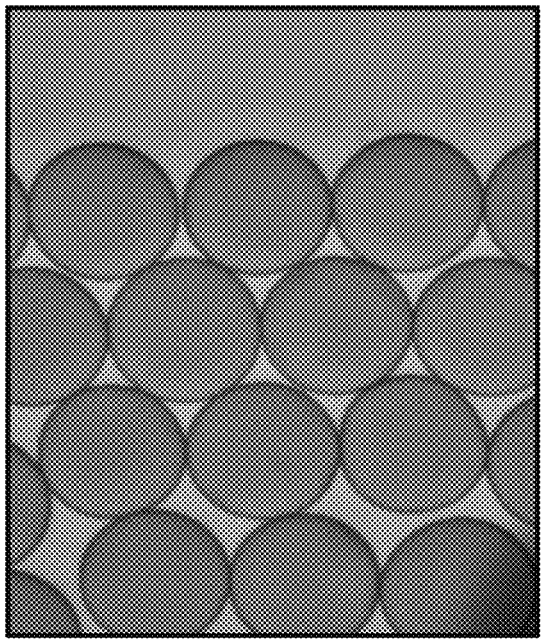
Figure 12:
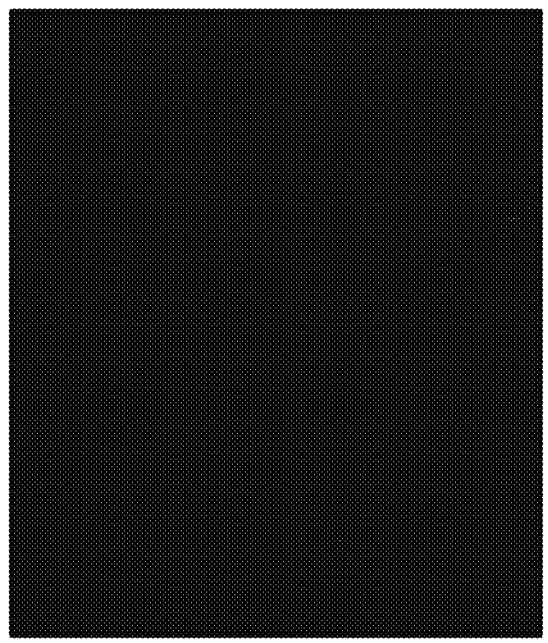

FIG. 12 shows a set of figures showing the measurement of colony size to estimate *E. coli* concentration, larger droplet size.

Figure 13:
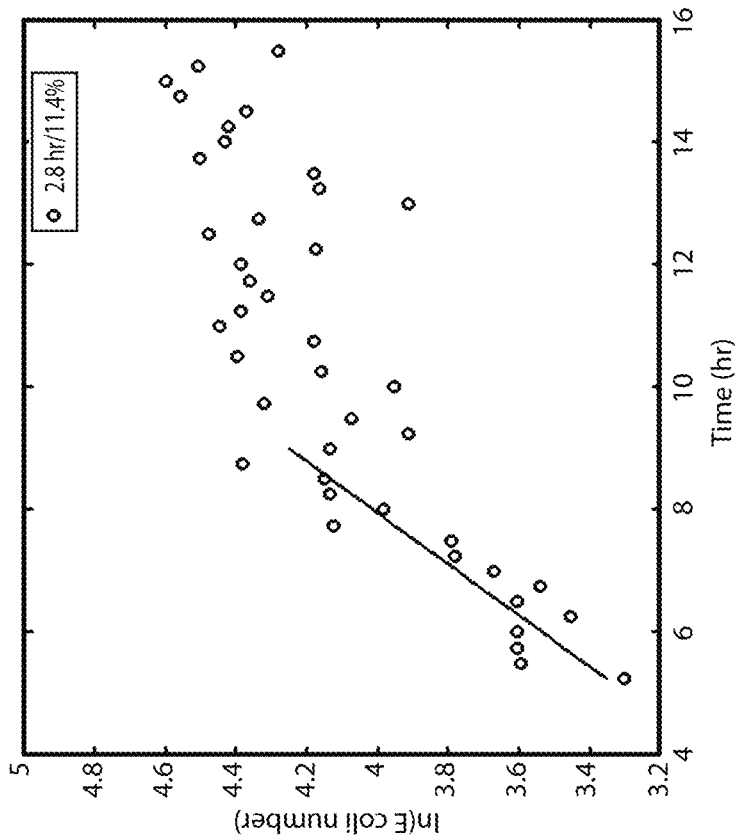
Figure 13:
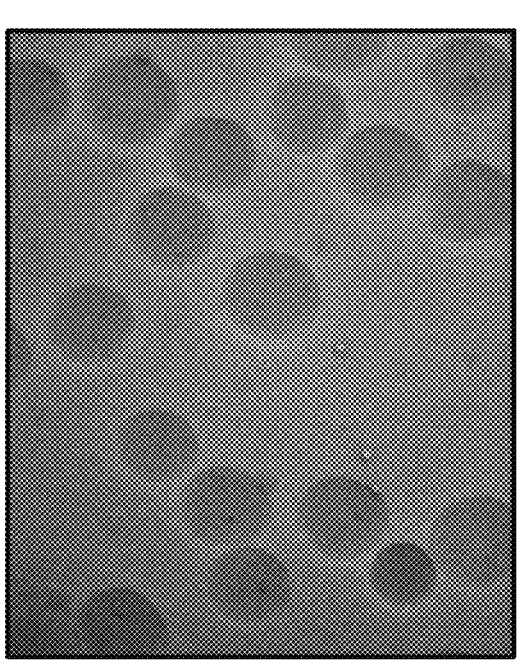
Figure 13:
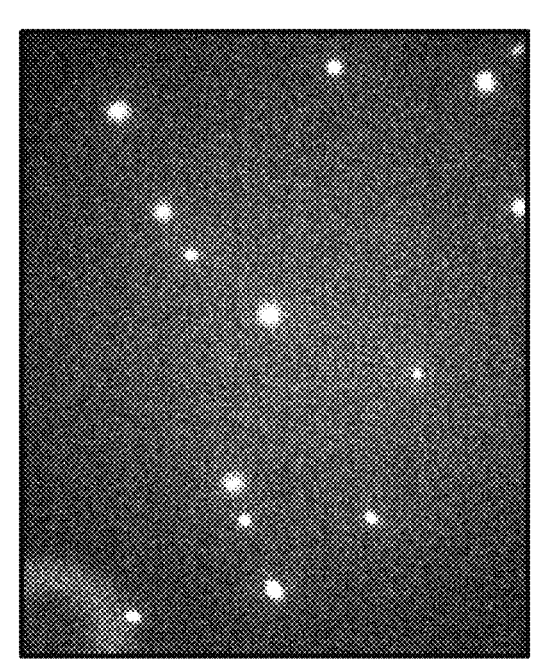

FIG. 13 shows a set of figures showing the measurement of colony size to estimate *E. coli* concentration, gel droplet in media.

Figure 14:
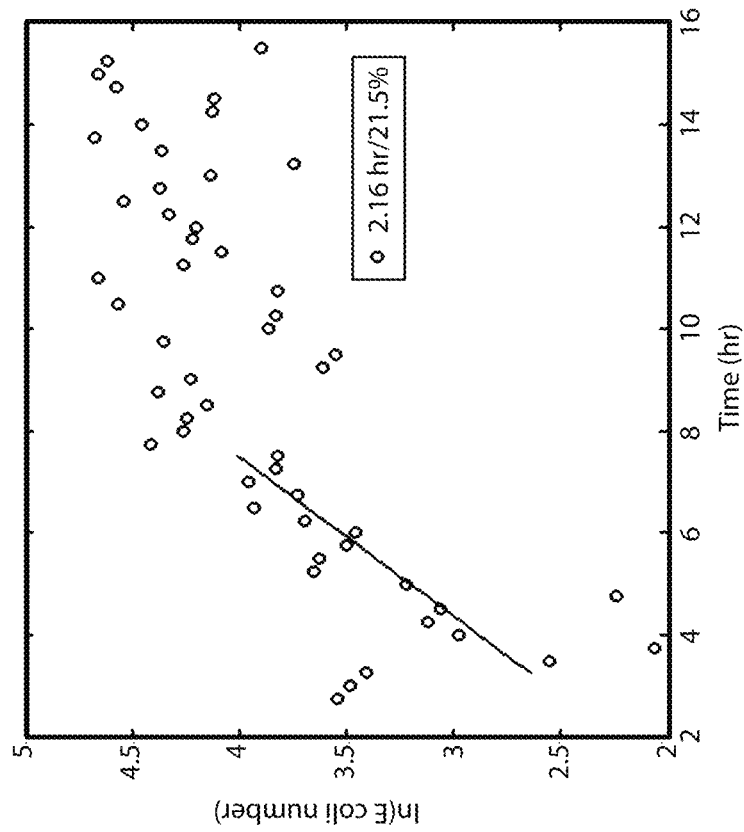
Figure 14:
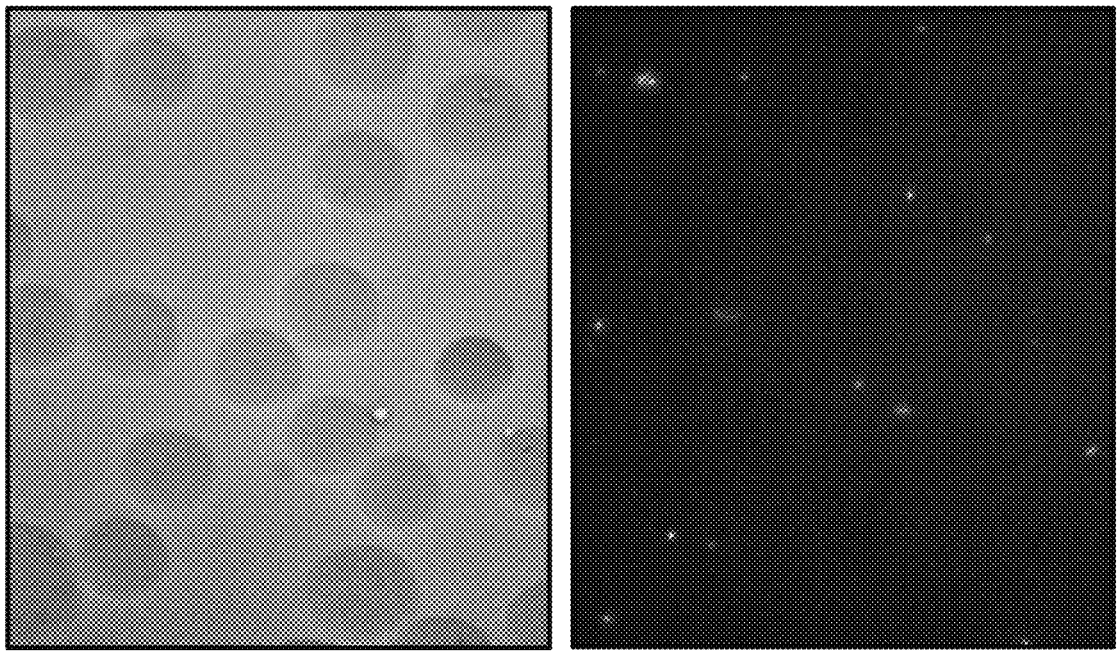

FIG. 14 shows a set of figures showing the measurement of colony size to estimate *E. coli* concentration, gel droplet in media.

Figure 15:
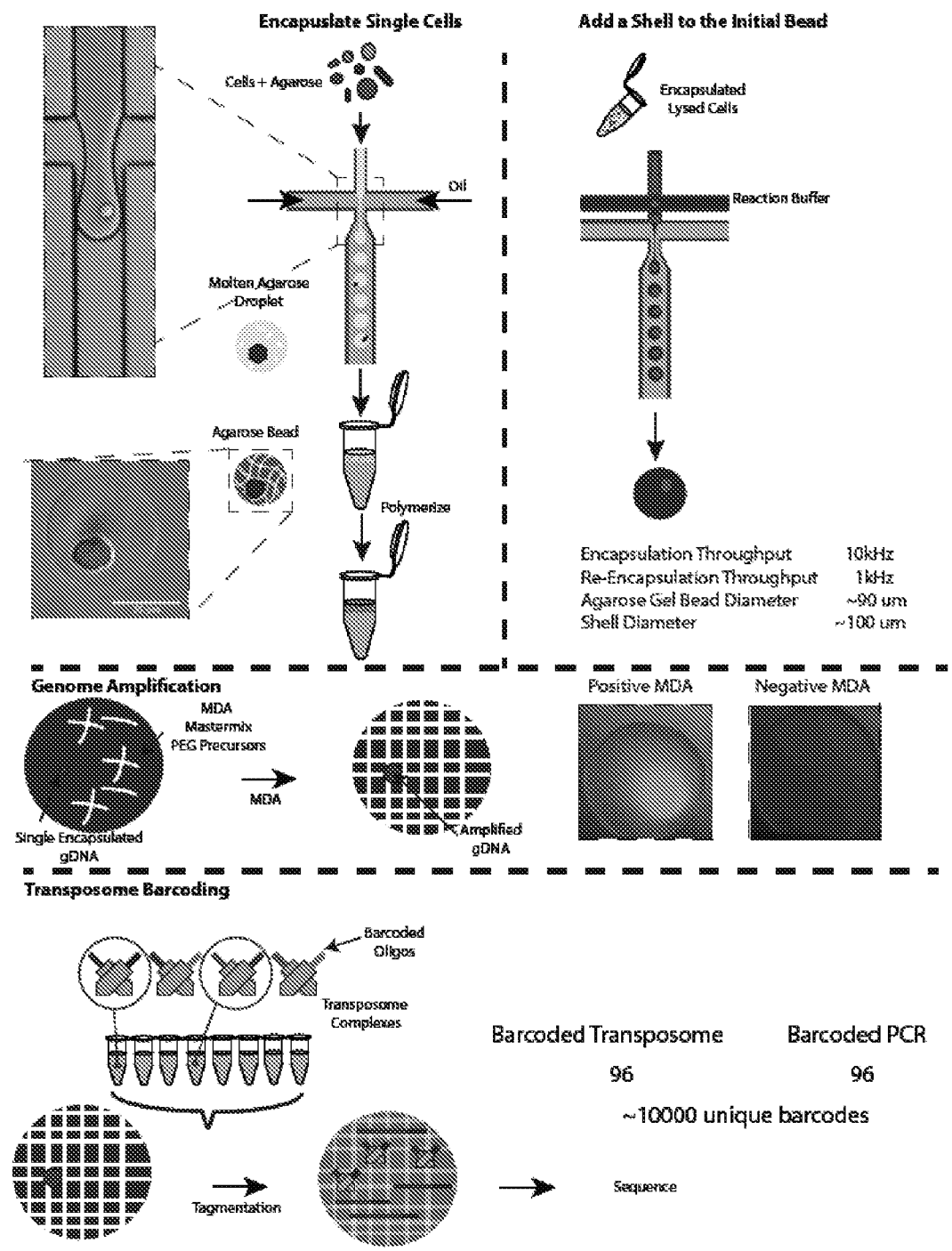

FIG. 15 shows a schematic providing an overview of bead droplet multiple displacement amplification (MDA), in accordance with certain example embodiments.

Figure 16:
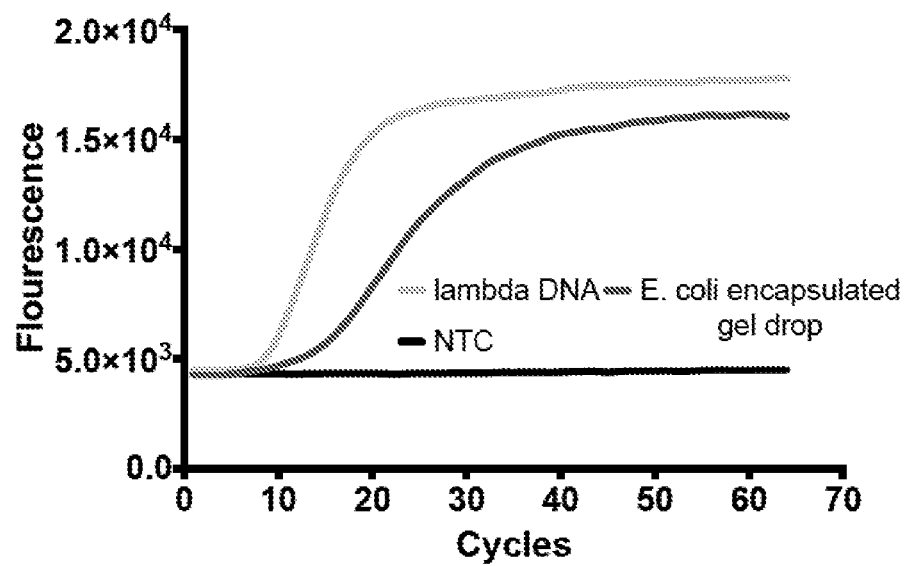

FIG. 16 shows a graph monitoring progression of MDA reactions in encapsulated beads loaded with 0.1 molecules of DNA, single cells, or nothing (NTC).

Figure 17:
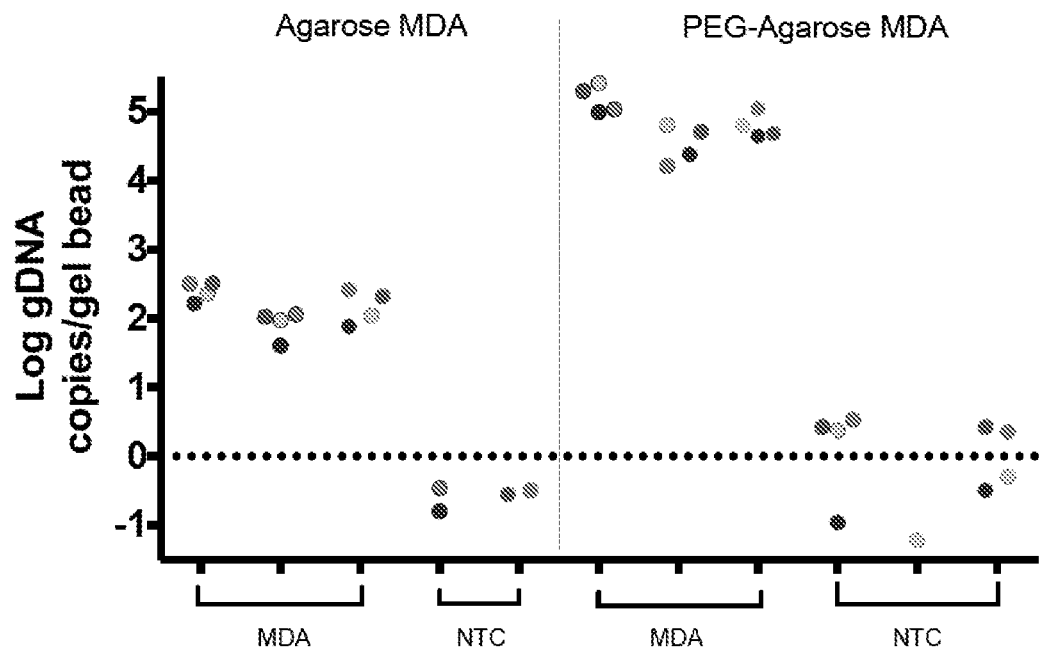

FIG. 17 shows a graph showing quantification of yields of MDA positive or NTC in agarose beads and agarose beads encapsulated in polyethylene glycol (PEG).

Figure 18:
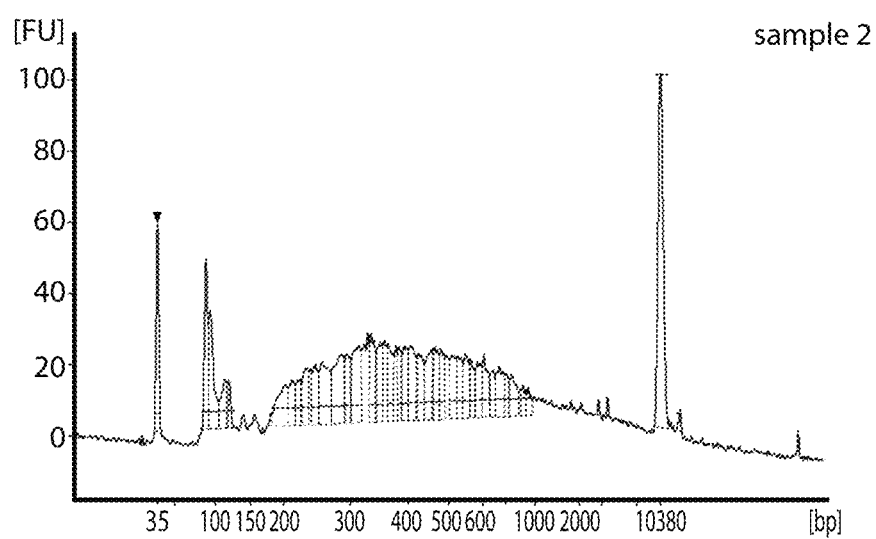

FIG. 18 shows graph of an example tagmented library generated through emulsion tagmentation, in accordance with certain example embodiments.

Figure 19:
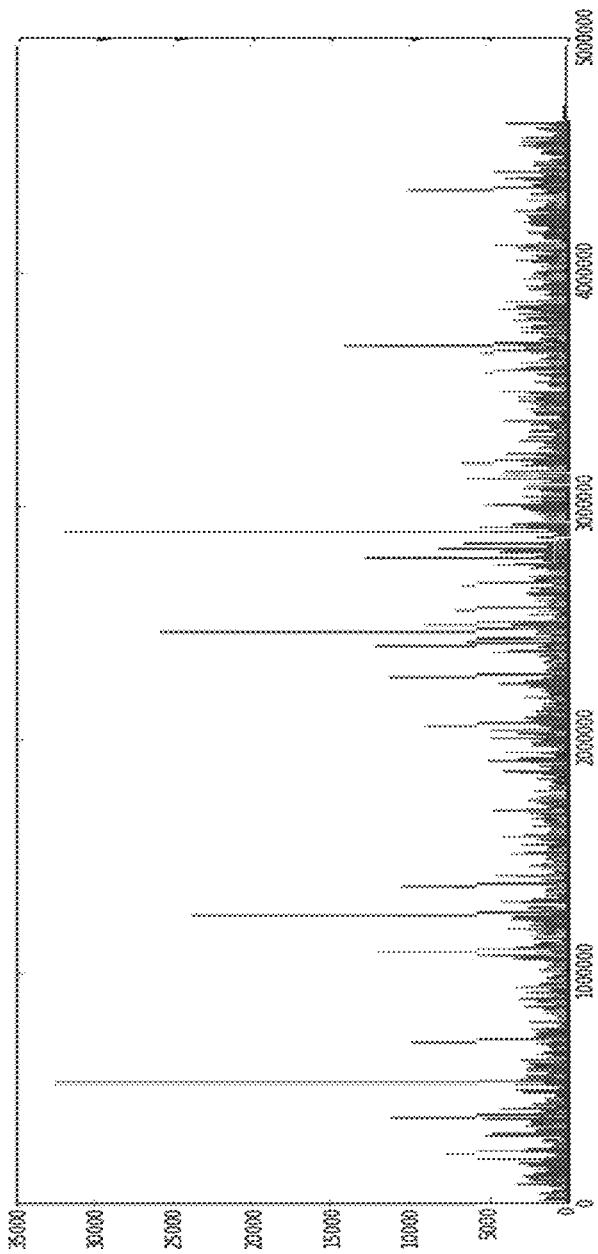

FIG. 19 shows a graph showing sequencing read coverage of the *E. coli* genome from 5 different beads, in accordance with certain example embodiments.

Figure 20:
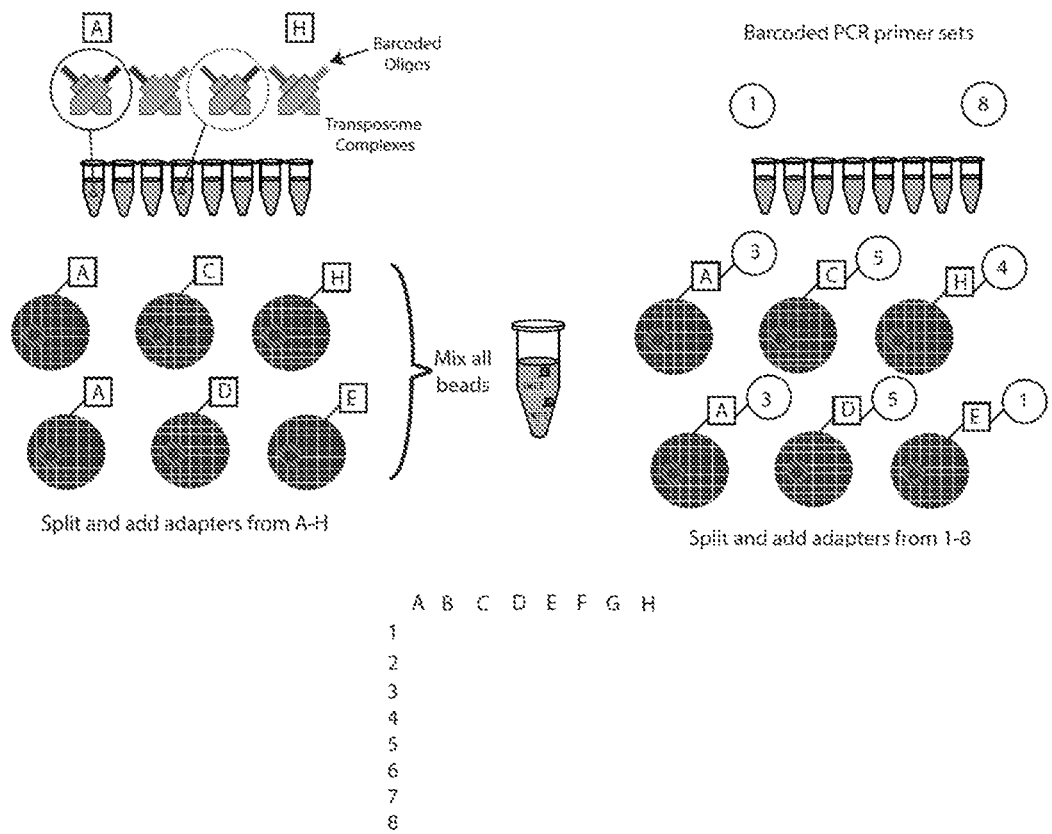

FIG. 20 shows a schematic showing a split and pool barcoding scheme for encapsulated bead.

Figure 21:
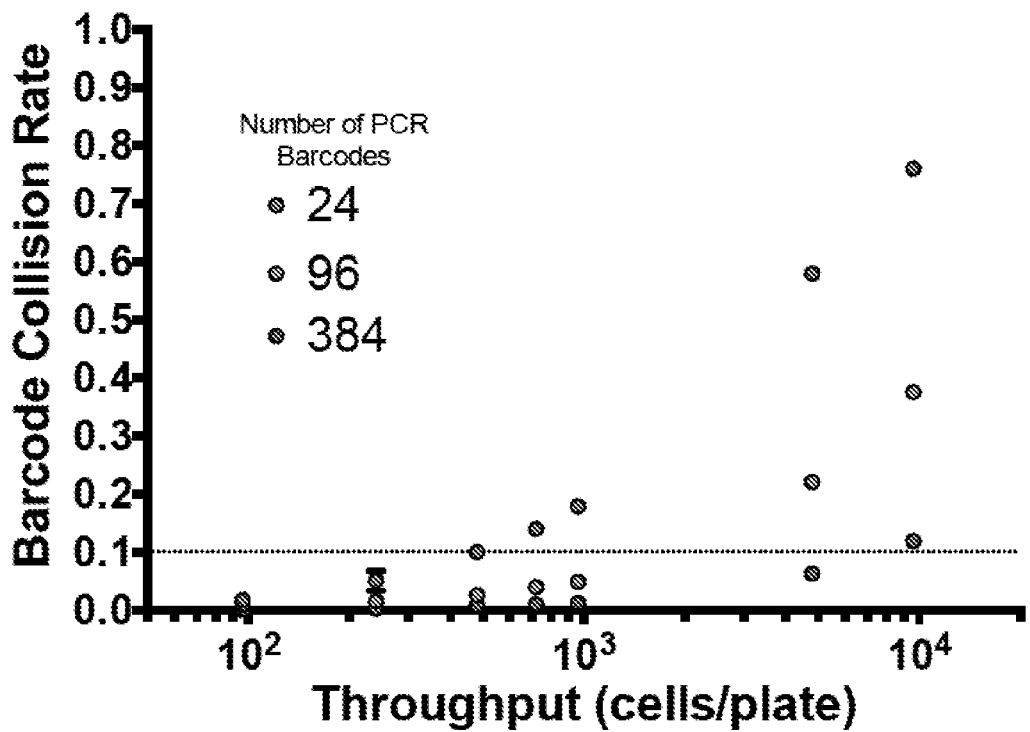

FIG. 21 shows a graph showing theoretical output versus barcode collision rate of split and pooled barcoded tagmentation and follow-up barcoded library amplification through PCT.

Figure 22:
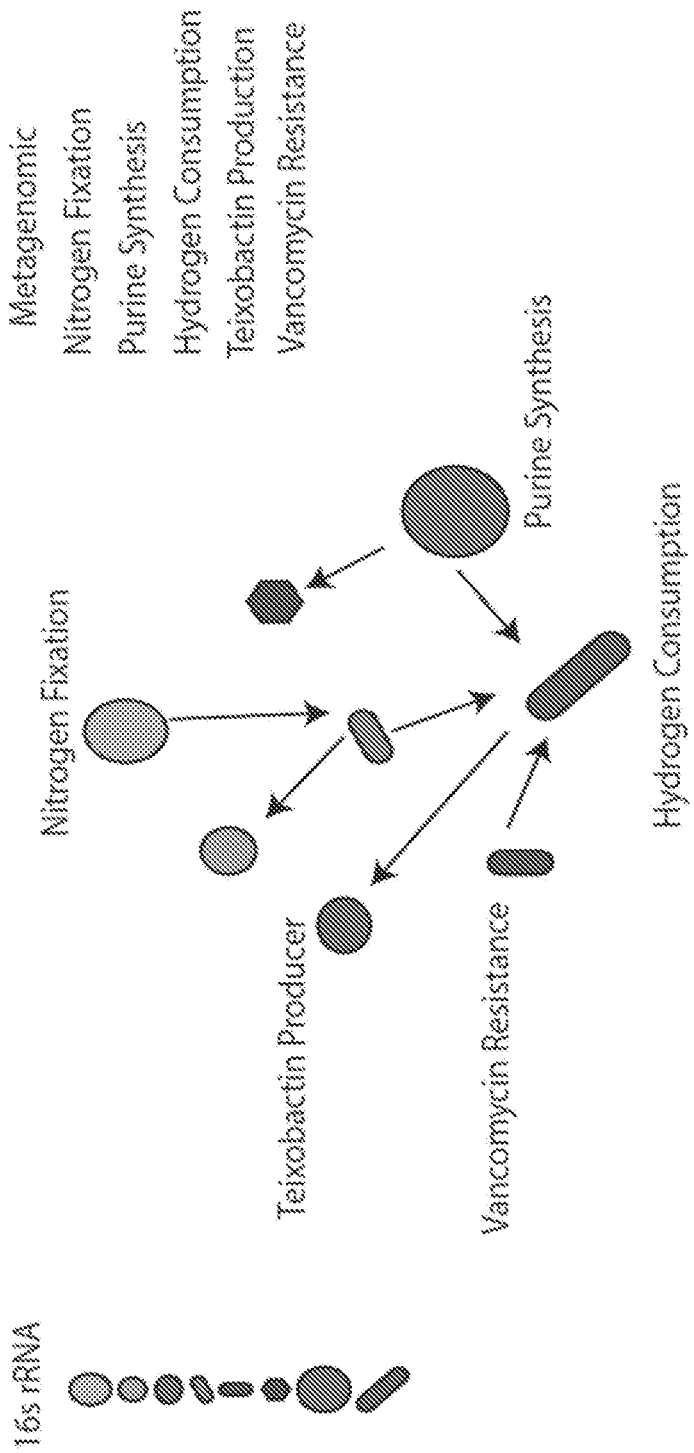

FIG. 22 shows a hypothetical where in certain cases the functional genes present may be more important than the identity of bacteria.

Figure 23:
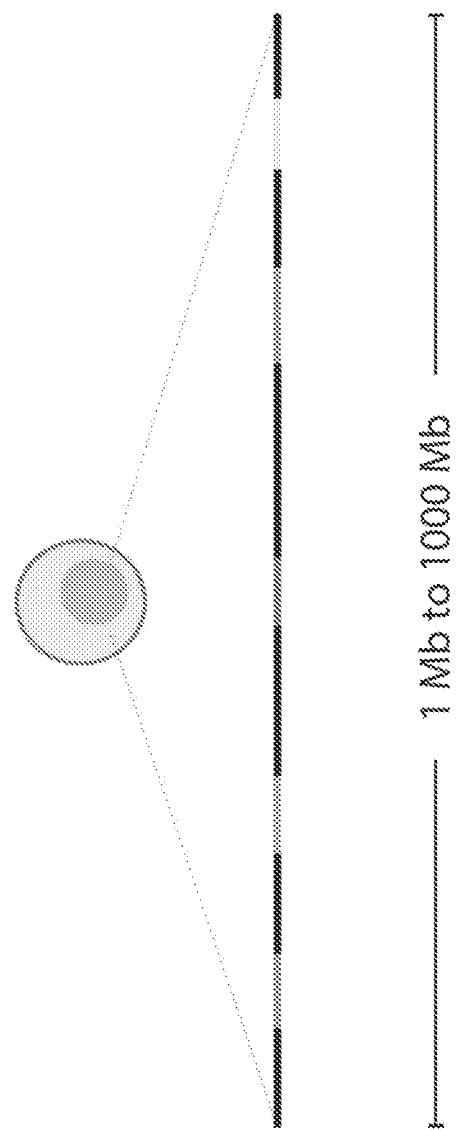

FIG. 23 shows a potential genome where interesting functional genes may be scattered, thus making it difficult to understand which collection of genes come from a single cell.

Figure 24:
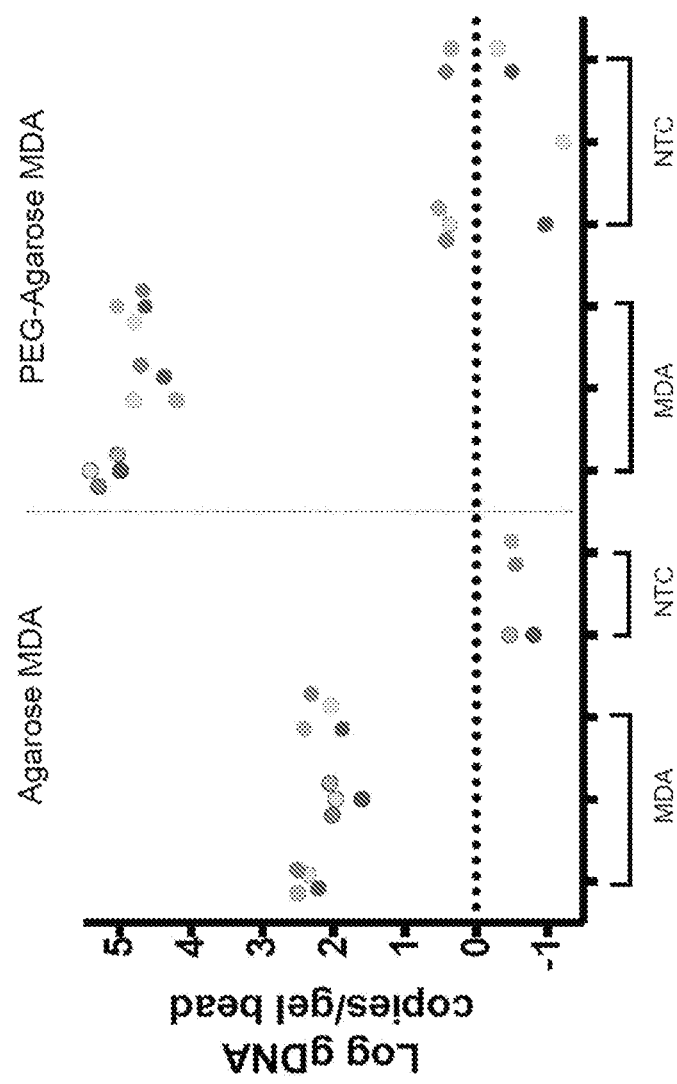

FIG. 24 shows MDA amplification in different gel scaffolds. In accordance with cetain example embodiments, an additional layer of PEG around the agarose beads may improves the DNA yield of single cells.

Figure 25:
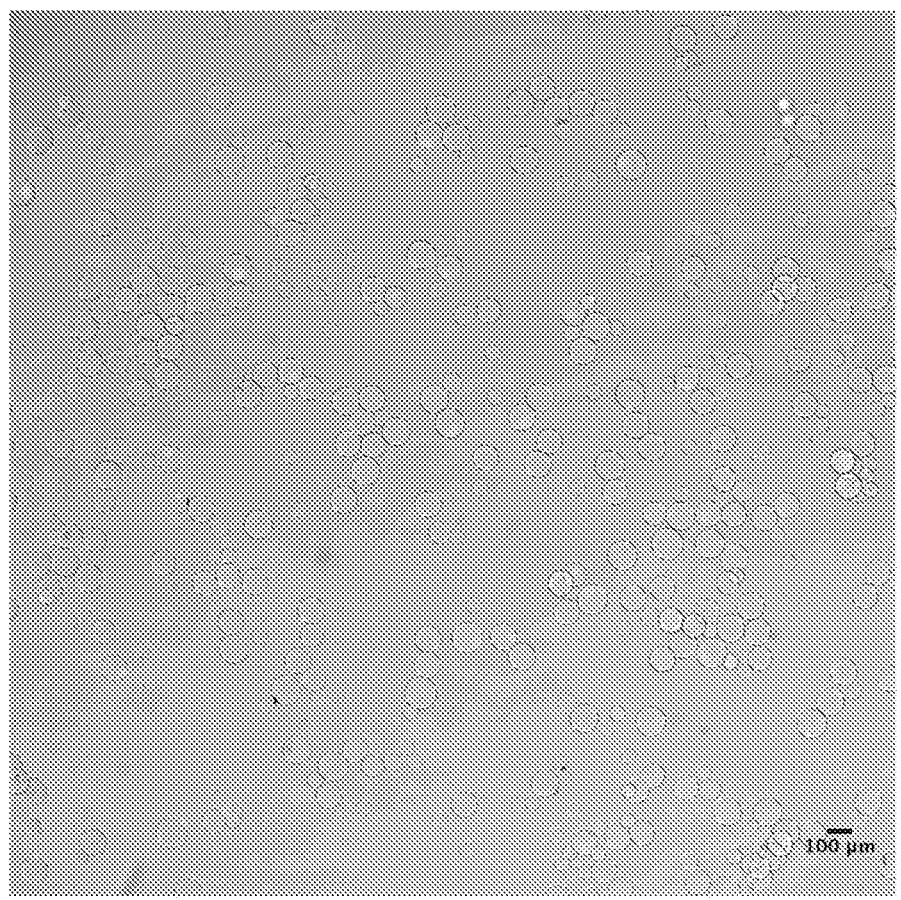

FIG. 25 shows MDA amplification in a pure acrylamide gel.

Figure 26C:
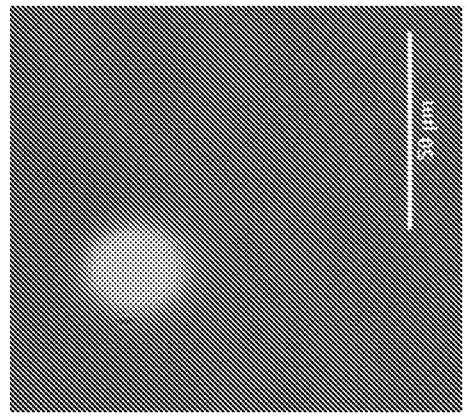
Figure 26B:
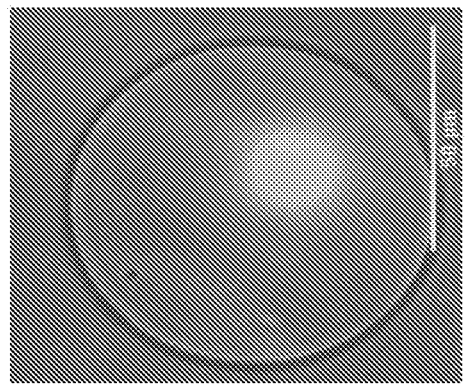
Figure 26A:
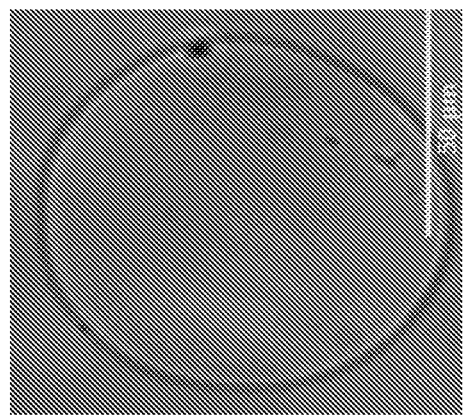

FIG. 26A-C shows DNA amplification in a degradable acrylamide gel. (A) no template control (NTC) (B) positive amplification of DNA in a single cell (C) after gel degradation, DNA cluster remains tightly clustered.

Figure 27B:
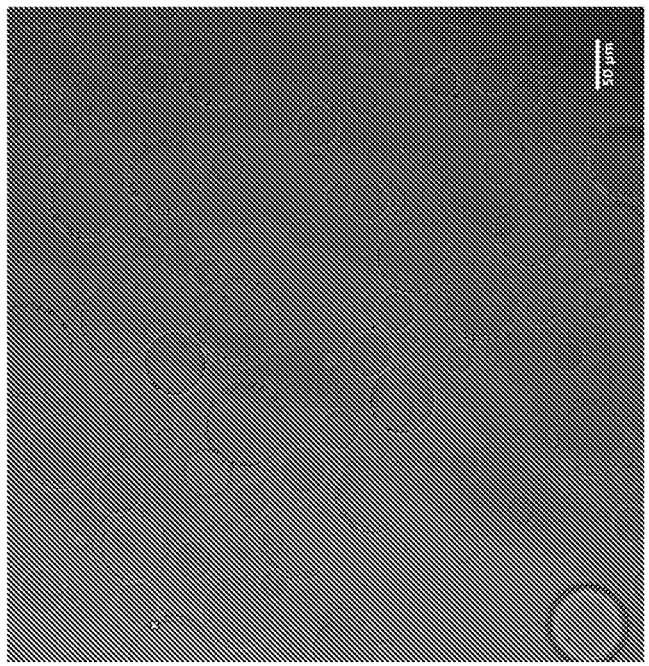
Figure 27A:
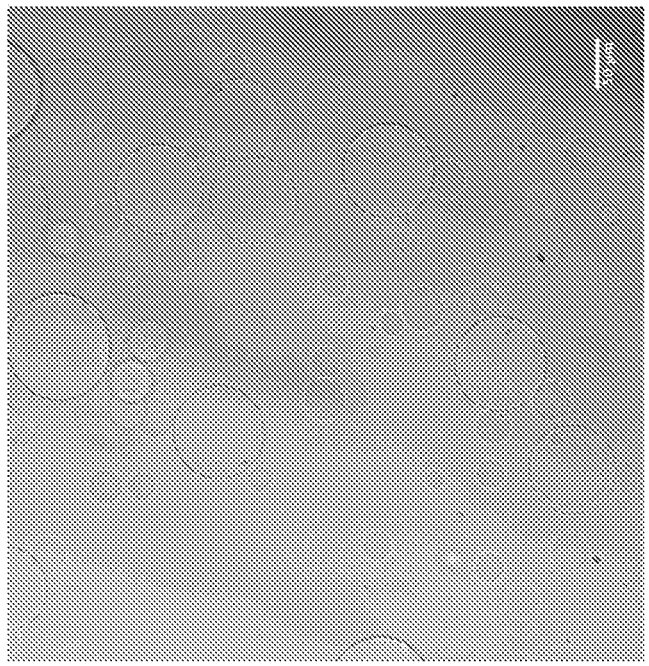
Figure 28A:
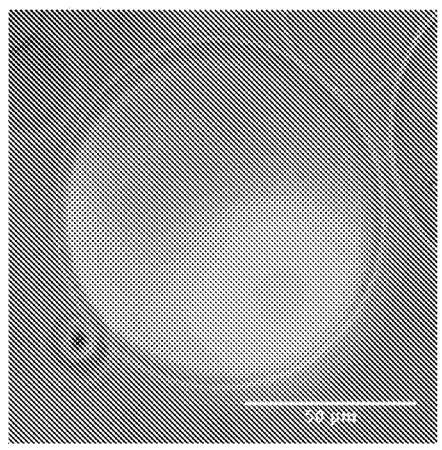
Figure 28B:
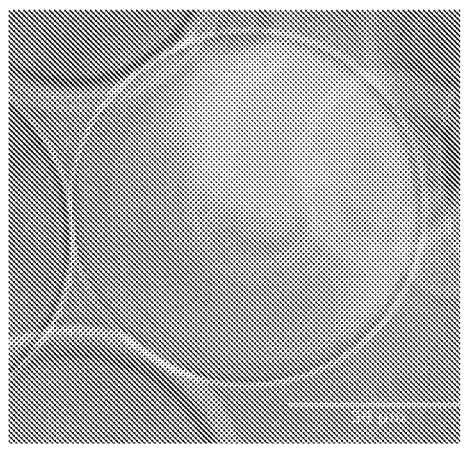
Figure 28C:
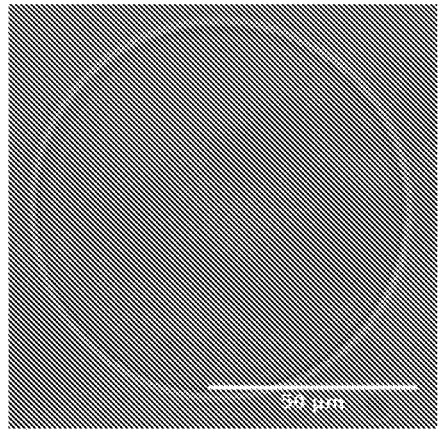
Figure 28D:
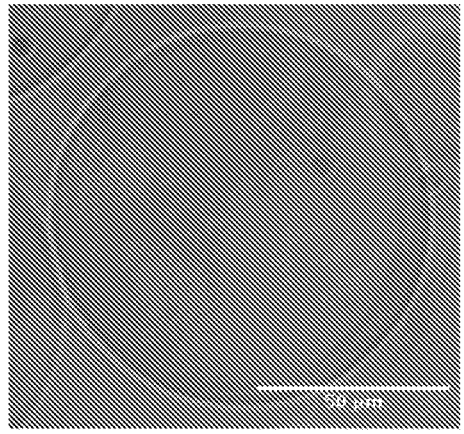

FIG. 27 (A and B) show examples of a degradable acrylamide inner gel with a non-degradable acrylamide outer gel.

FIG. 28A-D shows DNA amplification in a degradable core acrylamide gel. (A, B) show two positive samples where the DNA is trapped within the gel. (C, D) show two negatives that did not contain a single cell.

Figure 29:
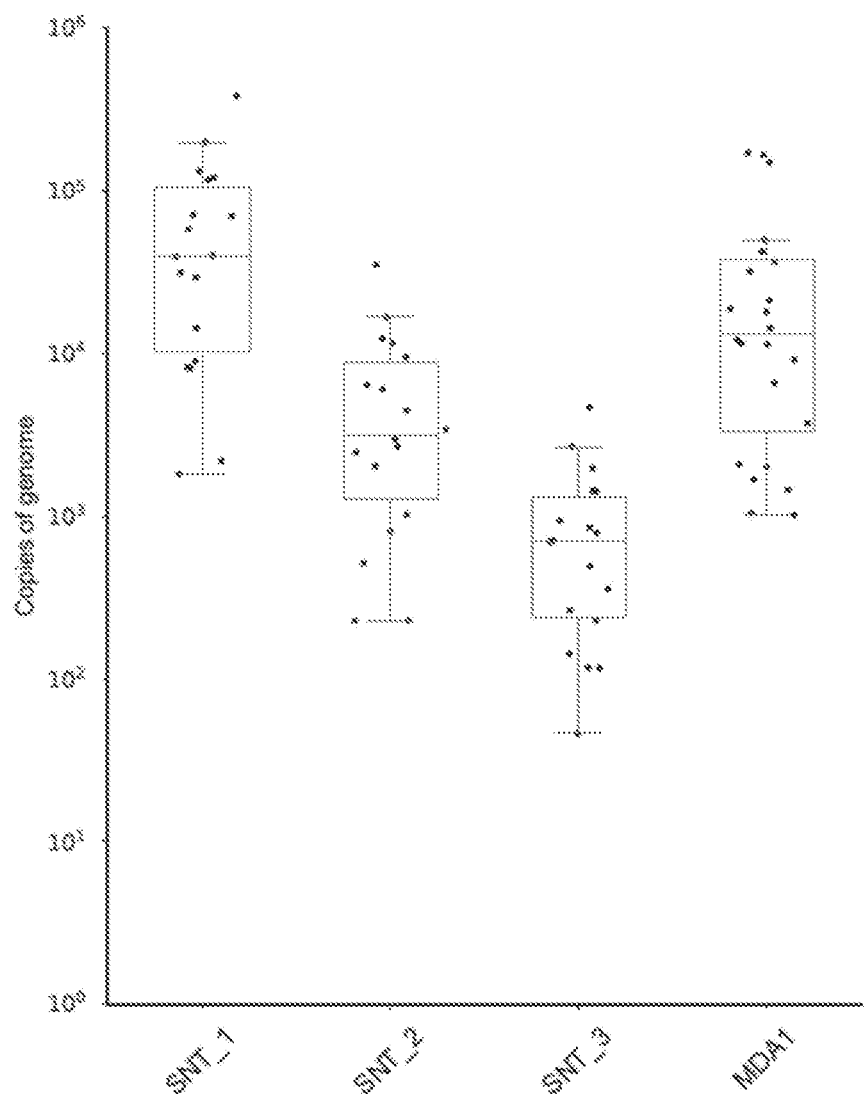

FIG. 29 shows DNA quantification post MDA and after successive washes. The DNA in the supernatant decreases below the level of DNA within an MDA positive bead.

Figure 30B:
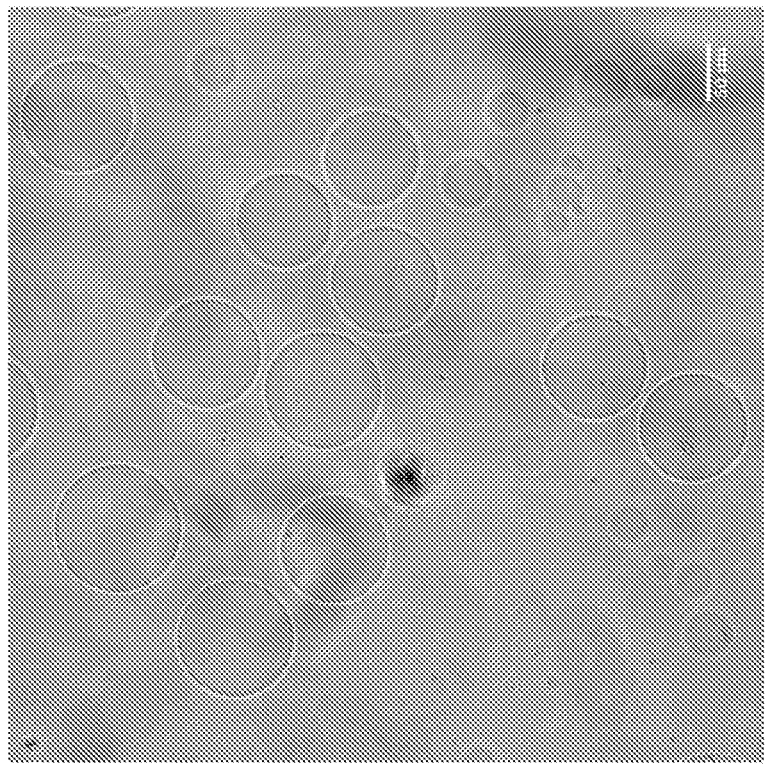
Figure 30A:
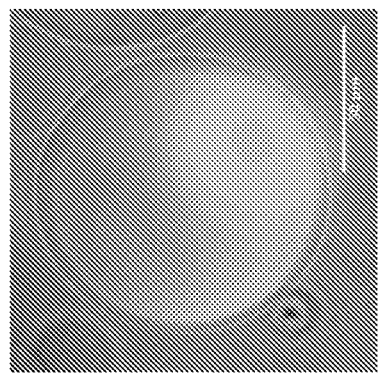
Figure 31C:
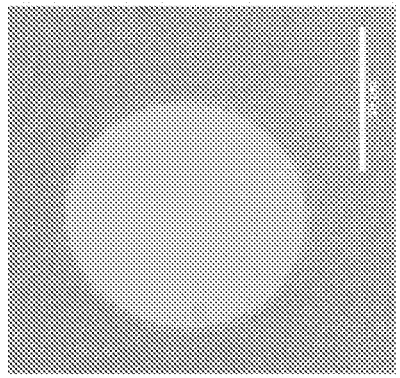
Figure 31E:
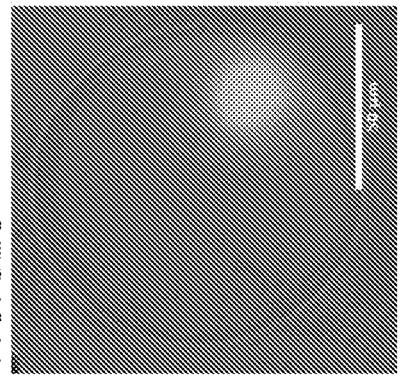
Figure 31B:
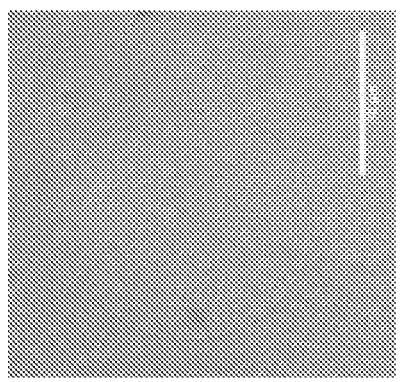
Figure 31D:
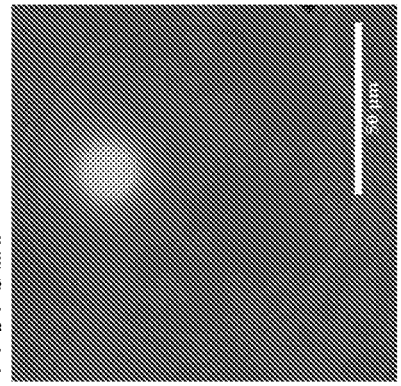
Figure 31A:
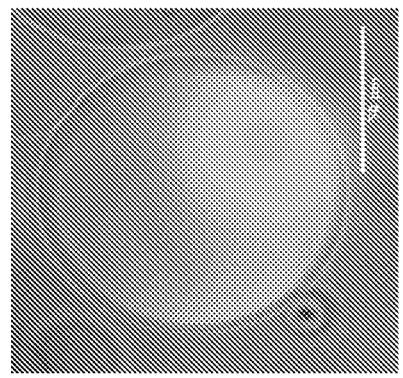

FIG. 30 (A and B) (A) positive MDA amplification (B) treatment with DNase 1 and S1 nuclease.

FIG. 31A-E (A) MDA positive amplification (B, C) DNA gel beads are treated with only S1 nuclease (D, E) DNA gel beads are treated with nextera enzyme.

Figure 32:
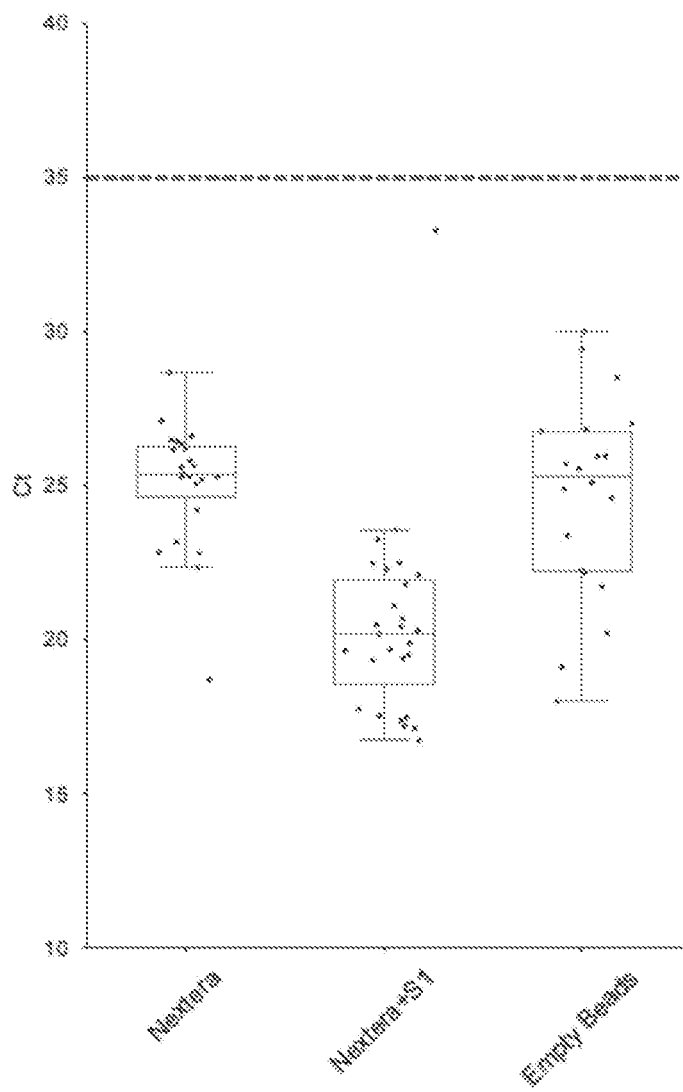

FIG. 32 shows Ct values for library prep PCR.

FIG. 33A-F shows tagmentation of fluorescent adapter (A, D) negative MDA (B, E) tagmentation of amplified DNA. (C, F) Treatment of MDA product with S1 nuclease.

Figure 34:
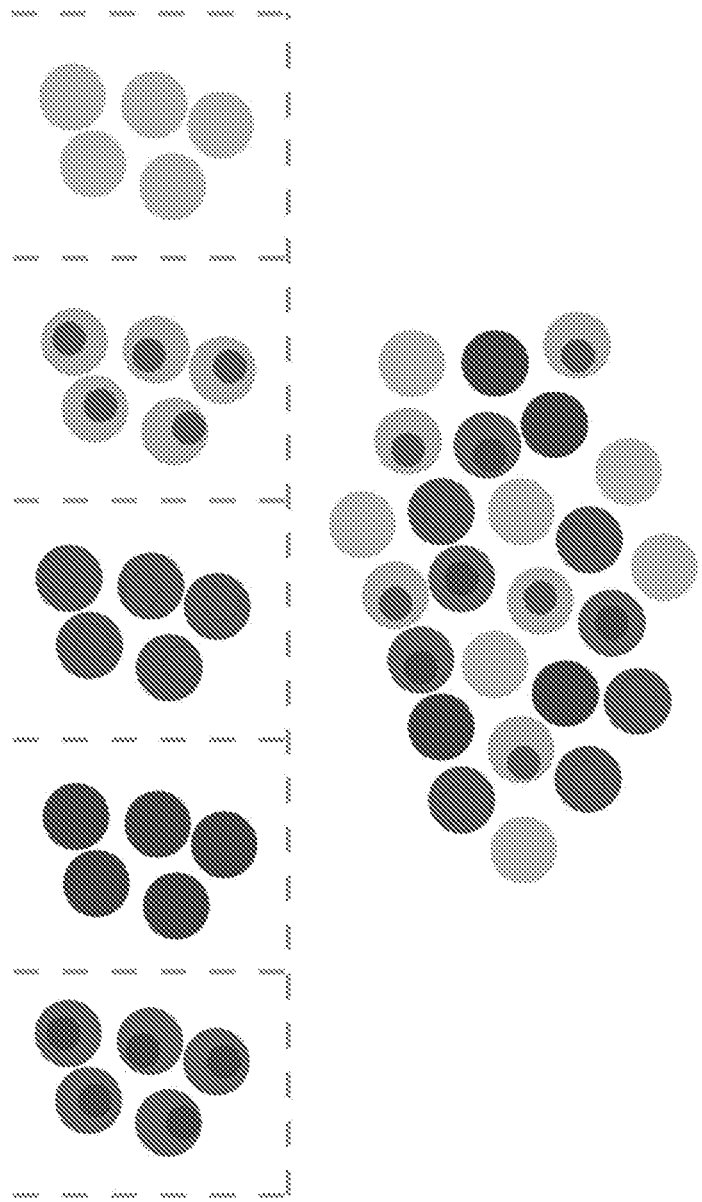

FIG. 34 shows an experimental design for measuring crosstalk in emulsion tagmentation barcoding.

Figure 35:
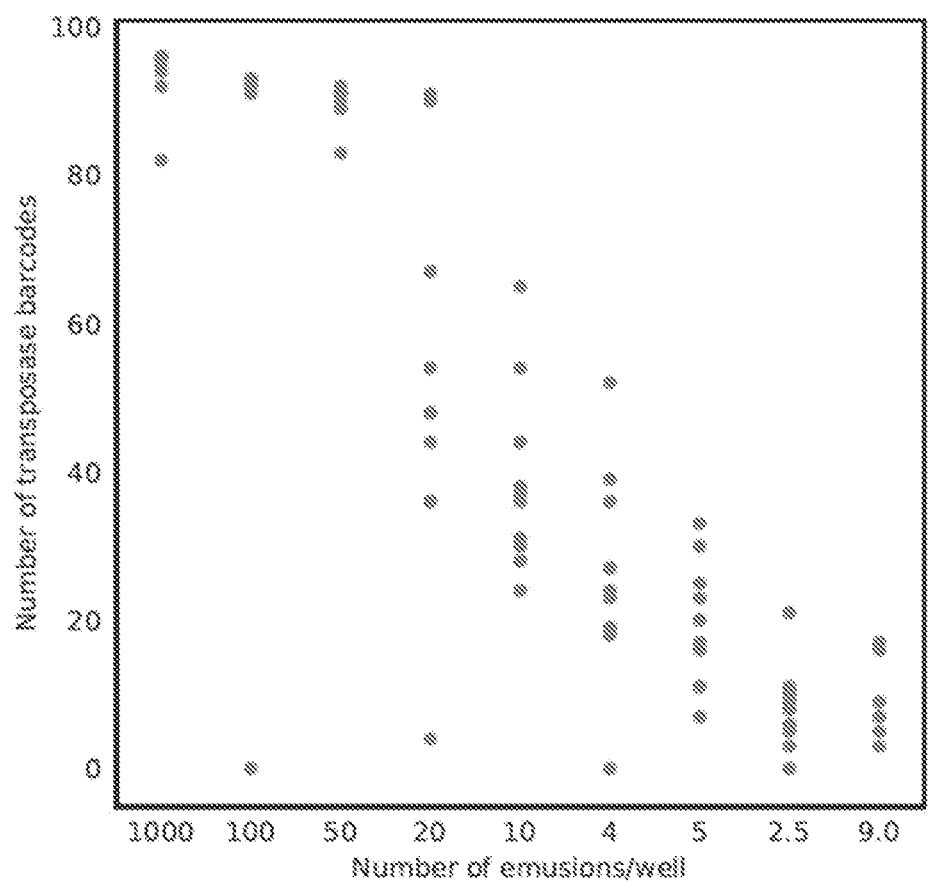

FIG. 35 shows the number of transposase barcodes identified for varying numbers of emulsions in PCR.

Figure 36:
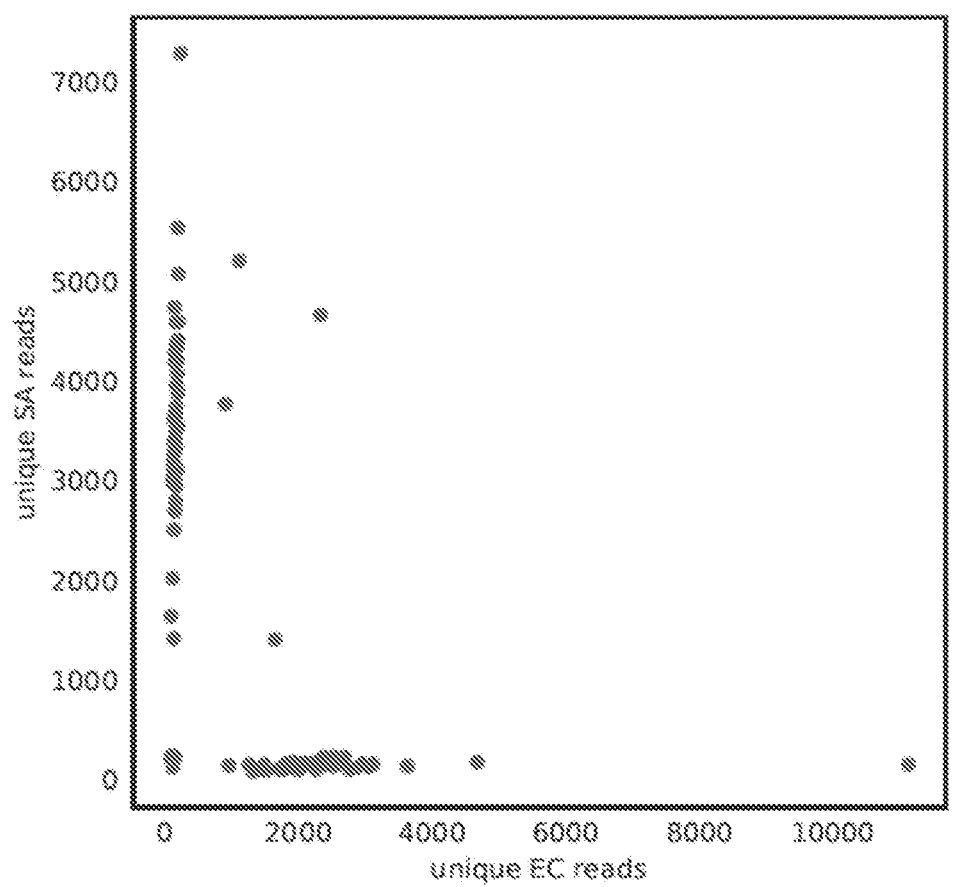

FIG. 36 shows a barnyard plot for cross contamination of tagmentation barcoding scheme.

Figure 37:
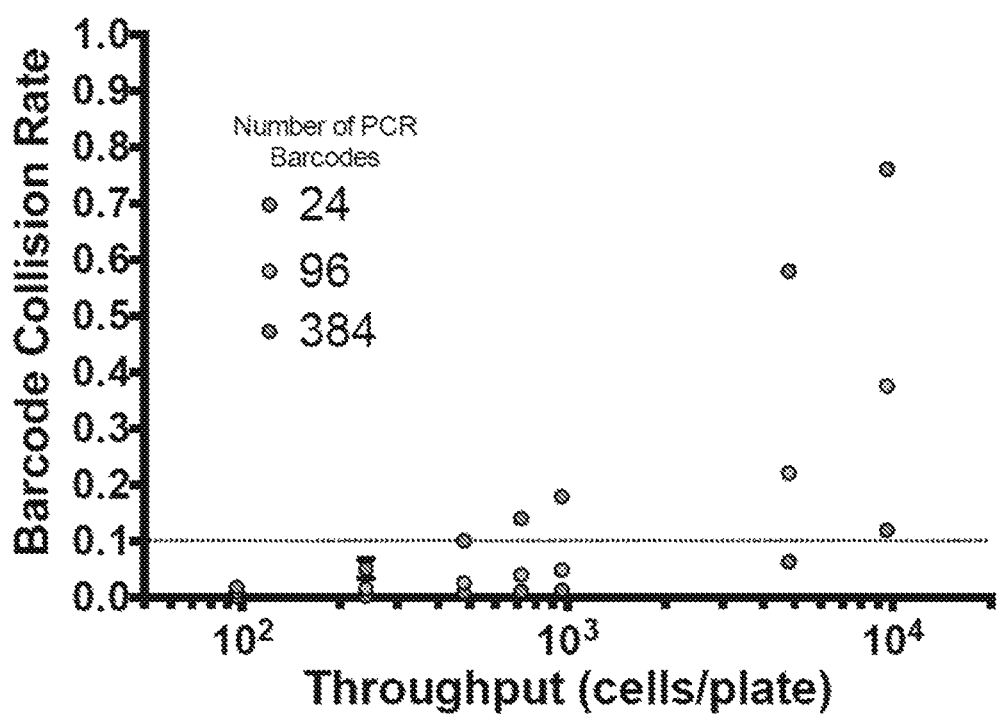

FIG. 37 shows a theoretical throughput for emulsion tagmentation barcoding with varying amounts of PCR primers and transposase primers.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2$^{nd}$ edition (1989) (Sambrook, Fritsch, and Maniatis); Molecular Cloning: A Laboratory Manual, 4$^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2$^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +1-5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide methods for multiplex screening of microscale biological systems for one or more biological functions. As used herein a microscale biological system refers to a cellular or acellular system capable of expressing one or more biomolecules exhibiting a biological function. In certain example embodiments, a microscale biological system may be a cell or population of cells. In certain example embodiments, a microscale biological system refers to an acellular system. In certain example embodiments, an acellular system may comprise one or more nucleic acid constructs encoding various nucleic acids and/or proteins. In general, each microscale biological system to be screened is placed within a series of nested individual discrete volumes, a first volume comprising the microscale biological system, and a second volume comprising one or more reporter elements for measuring a biological function of the microscale biological system.

As used herein, a "discrete volume" or "discrete space" may refer to a container, receptacle, or other defined volume or space that can be defined by properties that prevent and/or inhibit migration of molecules, particles and/or nucleic acid containing specimens. For example, a discrete volume or space may be defined by physical properties such as walls of a discrete well, tube, or surface of a droplet which may be impermeable or semipermeable. The discrete volume or space may also refer to a reaction unit or region within a larger volume, where that region is not defined by walls but rather is defined spatially by location within the larger volume. For example, the discrete volume or space may be chemically defined, diffusion rate limited defined, electromagnetically defined, or optically defined, or any combination thereof. By "diffusion rate limited" is meant volumes or spaces that are only accessible to certain species or reactions because diffusion constraints that would effectively limit the migration of a particular molecule, particle, or nucleic acid containing specimen from one discrete volume to another. By "chemically defined" is meant a volume or space where only certain molecules, particles, or nucleic acid containing specimens can exist because of their chemical or molecular properties. For example, certain gel beads may exclude certain molecules, particles, or nucleic acid containing specimens from entering the beads but not others by surface charge, matrix size, or other physical property of the gel bead. By "electro-magnetically defined" is meant volumes or spaces where the electro-magnetic properties of certain molecules, particles, or cells may be used to define certain volumes or spaces. For example, by capturing magnetic particles within a magnetic field or directly by magnets. By "optically defined" is meant volumes or spaces that may be defined by illuminating the volume or space with visible, ultraviolet, infrared, or other wavelengths of light such that only target molecules within the defined space or volume are detected.

In certain example embodiments, each individual microscale biological system may be identified by assigning each individual microscale biological system a unique barcode. This may be achieved by assigning a unique barcode to each individual discrete volume used in a screen and comprising a different microscale biological system. The individual discrete volumes may be pre-labeled with the unique barcode prior to loading each individual discrete volume with a microscale biological system, or the barcode may be introduced concurrently when loading the microscale biological systems. For example, small hydrogel beads labeled with a barcode may be added to each individual discrete volume. In certain example embodiments, a second barcode may be similarly used to identify the one or more reporter elements in an individual discrete volume. The barcode may be a nucleic acid-based barcode. The barcode may be an optical barcode.

A nucleic-acid based barcode is a short sequence of nucleotides (for example, DNA, RNA, or combinations thereof) that is used as an identifier for an associated molecule, such as a target molecule and/or target nucleic acid. A nucleic acid barcode can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. One or more nucleic acid barcodes can be attached, or "tagged," to a target molecule and/or target nucleic acid. This attachment can be direct (for example, covalent or non-covalent binding of the barcode to the target molecule) or indirect (for example, via an additional molecule, for example, a specific binding agent, such as an antibody (or other protein) or a barcode receiving adaptor (or other nucleic acid molecule). Target molecule and/or target nucleic acids can be labeled with multiple nucleic acid barcodes in combinatorial fashion, such as a nucleic acid barcode concatemer. Typically, a nucleic acid barcode is used to identify a target molecule and/or target nucleic acids as being from a particular compartment (for example a discrete volume), having a particular physical property (for example, affinity, length, sequence, etc.), or having been subject to certain treatment conditions. Target molecule and/or target nucleic acid can be associated with multiple nucleic acid barcodes to provide information about all of these features (and more). Methods of generating nucleic acid-barcodes are disclosed, for example, in International Patent Application Publication No. WO/2014/047561.

Optically detectable barcodes are barcodes that can be detected with light or fluorescence microscopy. In certain example embodiments, the optical barcodes may comprise a sub-set of fluorophores or quantum dots of distinguishable colors from a set of defined colors. In certain example embodiments, beads are labeled with different ratios of dyes to form the set of defined colors from which the optical barcodes may be derived. For example, the beads may be polystyrene beads labeled with biotin conjugated dyes. Alternatively, the optical barcodes may be derived using a combination of optically detectable objects. For example, an optical barcode may be defined from a set of objects that can vary in size, shape, color, or any combination thereof that is distinguishable by light or fluorescence microscopy.

In certain example embodiments, microscale biological systems are first encapsulated in a bead by causing droplets to form around each individual microscale biological system. The fluid used to form the droplet comprises one or more polymers or polymer precursors. After successful droplet formation, the one or more polymers are then polymerized to form solid or semi-solid beads encapsulating the microscale biological system. For example, the polymers may be maintained at an elevated temperature, or under other physical conditions, that will maintain the polymer composition in a liquid or molten state. After droplet formation, the physical condition may be removed and/or changed such that polymerization of the polymer may occur. In some example embodiments, polymerization may be induced by addition of a polymerizing agent that triggers polymerization of polymer precursors, such as a free-radical generating agent. The bead may be further encapsulated in a second polymer in the same way. The polymer used to form the outer capsule may be the same or different from the polymer used to form the inner bead. In certain example embodiments, the inner bead may range in size from (diameter) 20 µm to 60 µm, and the outer capsule may range in size from 60 µm to 100 µm diameter.

These encapsulated beads may then be screened for one or more biological functions, at least in part, by detecting the readout of the one or more reporter elements. In certain example embodiments, the biological function may be determined by observation of the encapsulated beads using light or fluorescent microscopy, or similar imaging technique, in place of or in addition to other readouts of the one or more reporter elements.

In certain example embodiments, the methods may further comprise sorting the encapsulated beads based, at least in part, on the detected readout of the one or more reporter elements and analyzing the sorted encapsulated beads identified as having the one or more desired biological functions. The method may further comprise isolating and/or purifying said biological agents and optionally further characterizing the isolated biological agents. In certain example embodiments, the method may comprise sequencing of the microscale biological system and/or expression products of the microscale biological system.

Figure 1:
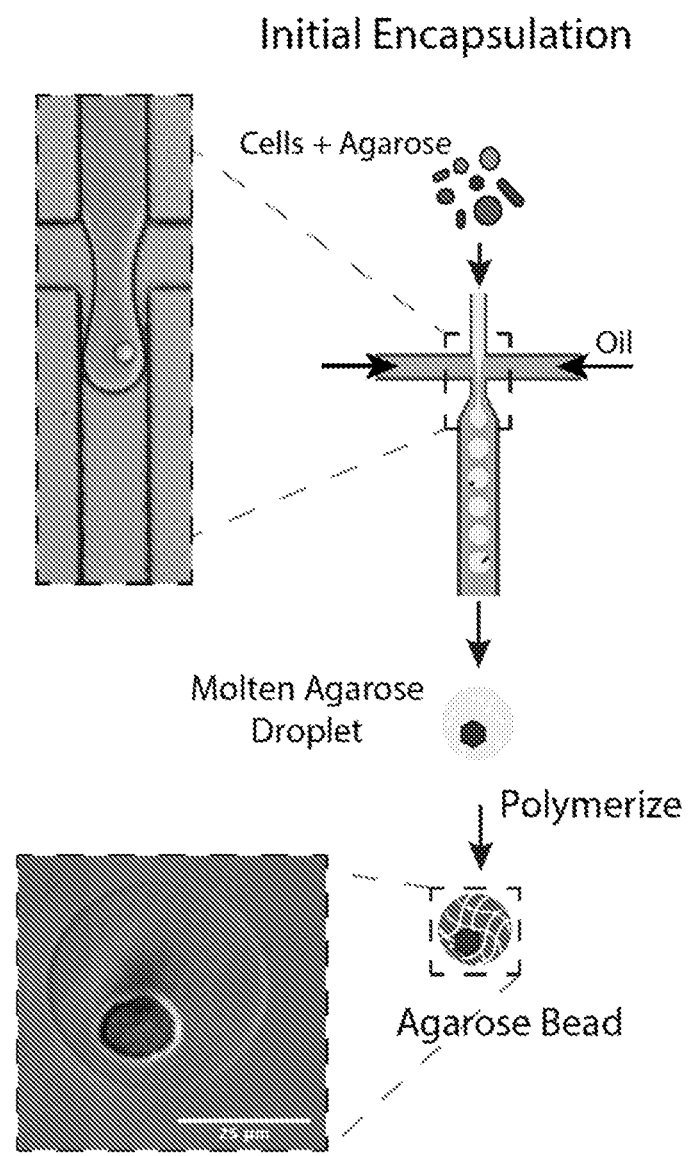
FIG. 1 shows a schematic representation of an exemplary overall scheme for single cell screening of biological function, in accordance with certain example embodiments. (Left) Device design for initial encapsulation of screening strain within molten agarose followed by gelation and incubation. The top inset shows an example of a droplet about to bud off due to the shear from the continuous (oil) phase. The bottom inset represents in a single *E. coli* cell which grew from an overnight culture. The screening strain (actinomycetes for validation) will be similarly encapsulated. (Right) The screening strain initially encapsulated can now be re-encapsulated within another layer of molten agarose. This layer will contain a reporter strain, here a multi-drug resistant *E. coli* with an engineered fluorescent stress response, which is used to assay for metabolite production. The top inset shows the device design for re encapsulation. The middle inset shows a gel droplet containing magnetic beads that was successfully re-encapsulated, which is possible at super poisson loading. Lastly, the analysis of each individual gel droplet is possible on a flow cytometer, which allows for gating and sorting.
Figure 2:
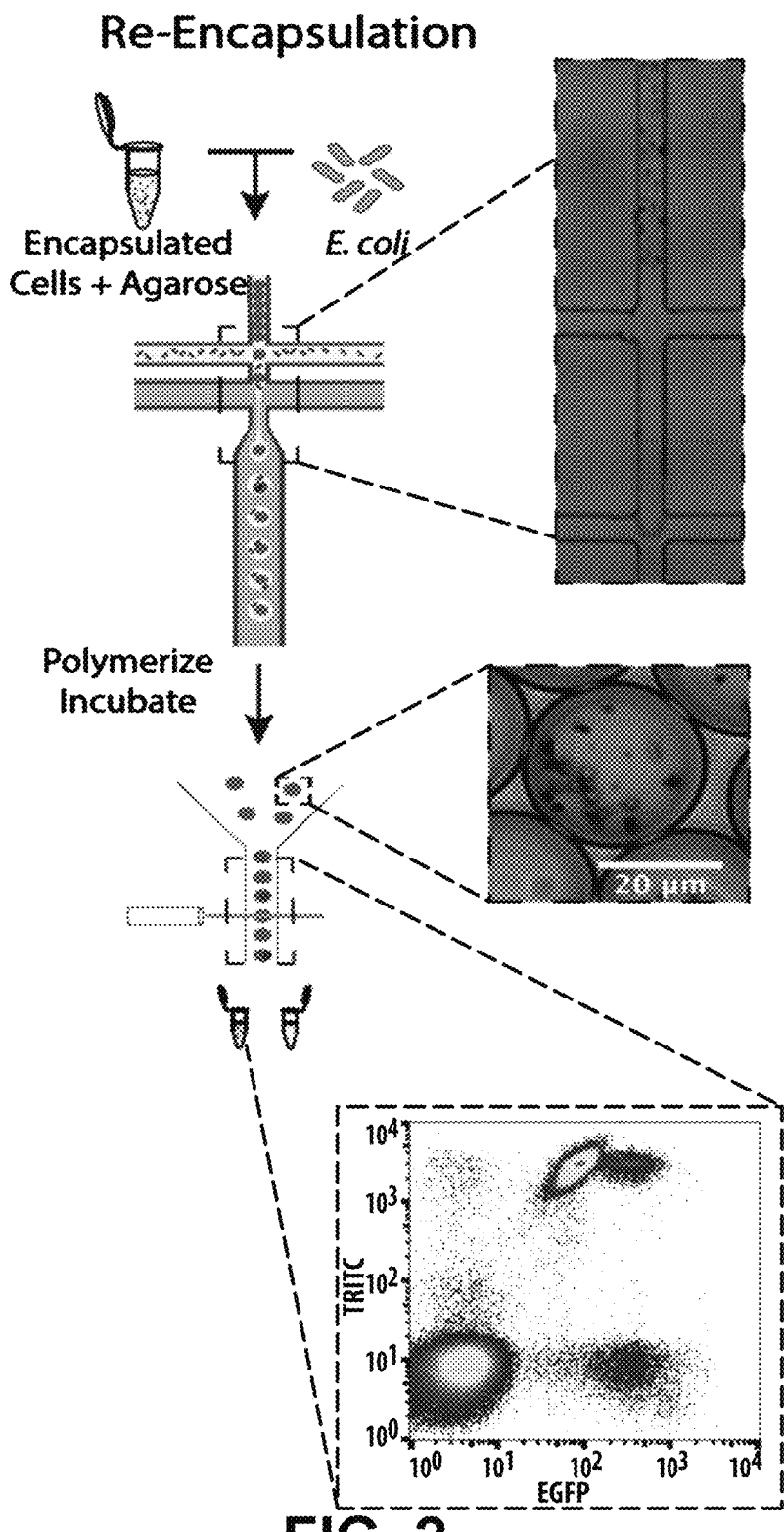
FIG. 2 shows a schematic representation of an exemplary overall scheme showing how a screening strain initially encapsulated can now be re-encapsulated within another layer of molten agarose. This layer will contain a reporter strain, here a multi drug resistant *E. coli* with an engineered fluorescent stress response, which is used to assay for metabolite production. The top inset shows the device design for re encapsulation. The middle inset shows a gel droplet containing magnetic beads that was successfully re-encapsulated, which is possible at super poisson loading. Lastly, the analysis of each individual gel droplet is possible on a flow cytometer, which allows for gating and sorting.
Figure 3:
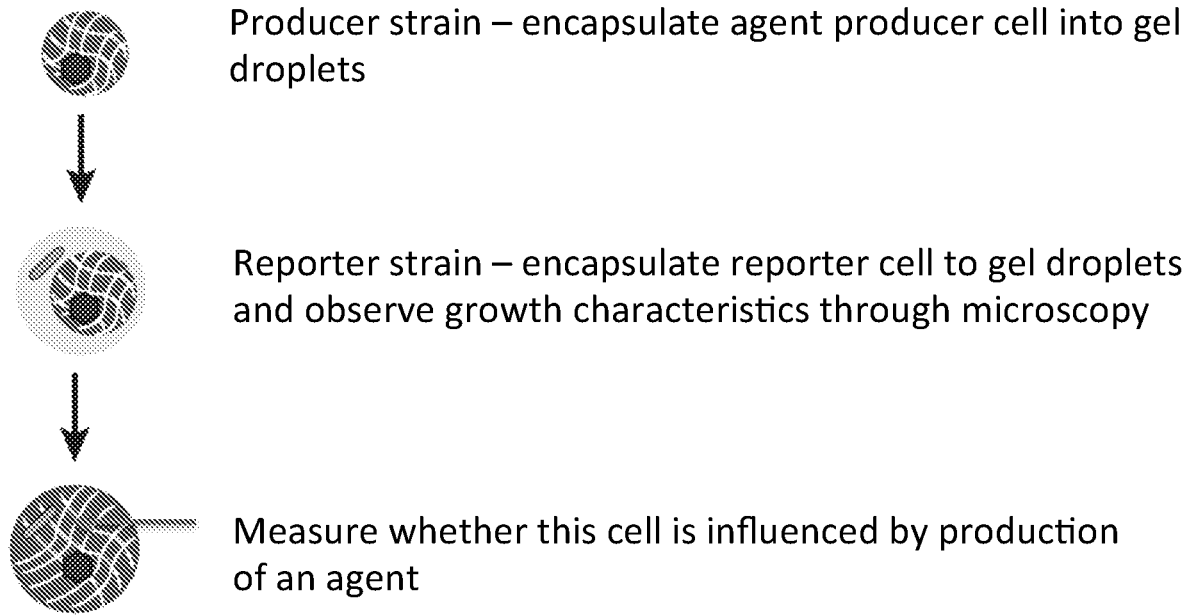
FIG. 3 shows a schematic representation of an example double encapsulation method for detecting production of an agent of biological interest from a microscale biological system using a reporter cell, in accordance with certain example embodiments.
Figure 4:
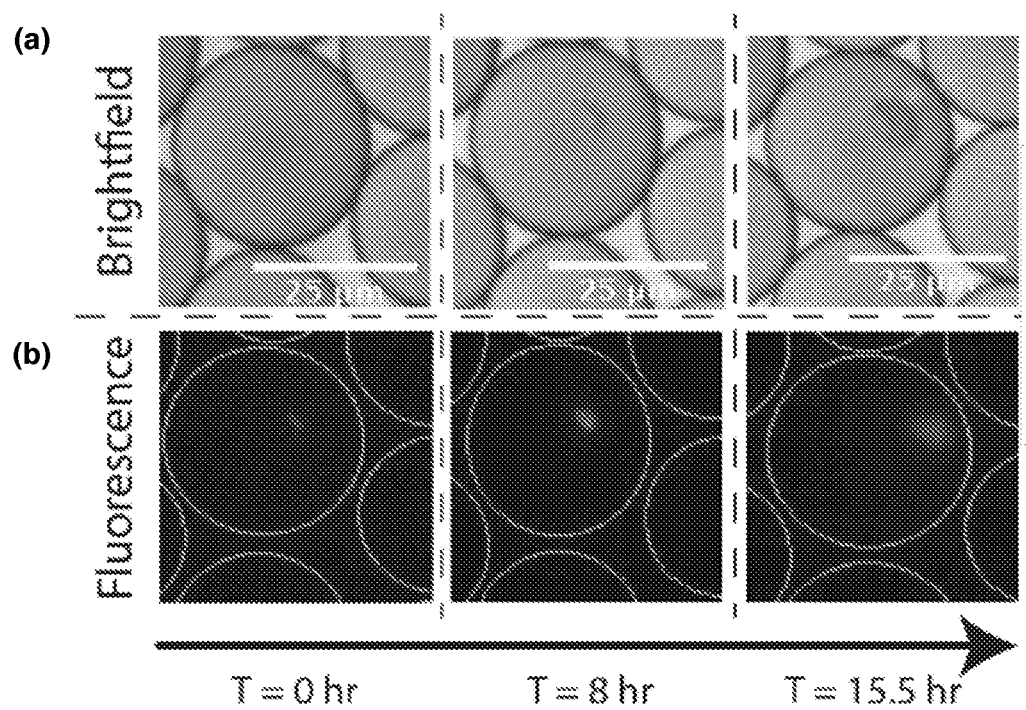
FIG. 4 shows a set of digital tracking the growth of individual cells through both (A) brightfield and (B) fluorescence microscopy. Viability and growth measurements of *E. coli* encapsulated within gel droplets. Tracking of individual cells was done through fluorescence microscopy at room temperature. Colony growth may be visualized through both brightfield and fluorescence microscopy.
Figure 5:
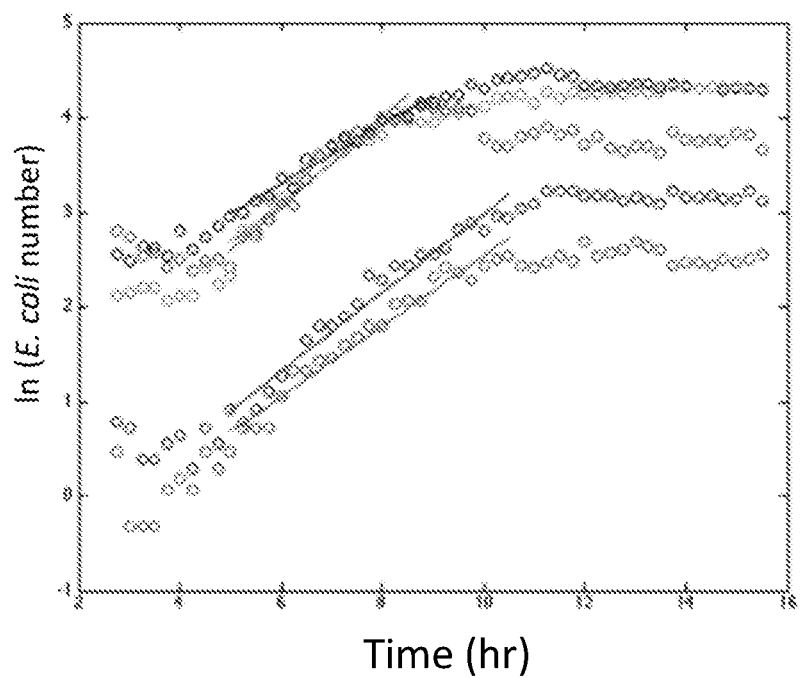
FIG. 5 shows a graph showing growth curves for multiple encapsulated cells. There is spread within average single cell growth rates which is consistent both with literature observations of single cell growth as well as bulk cultures of *E. coli*. Percentage next to value in inset are fitting uncertainties of the growth rate.
Figure 6:
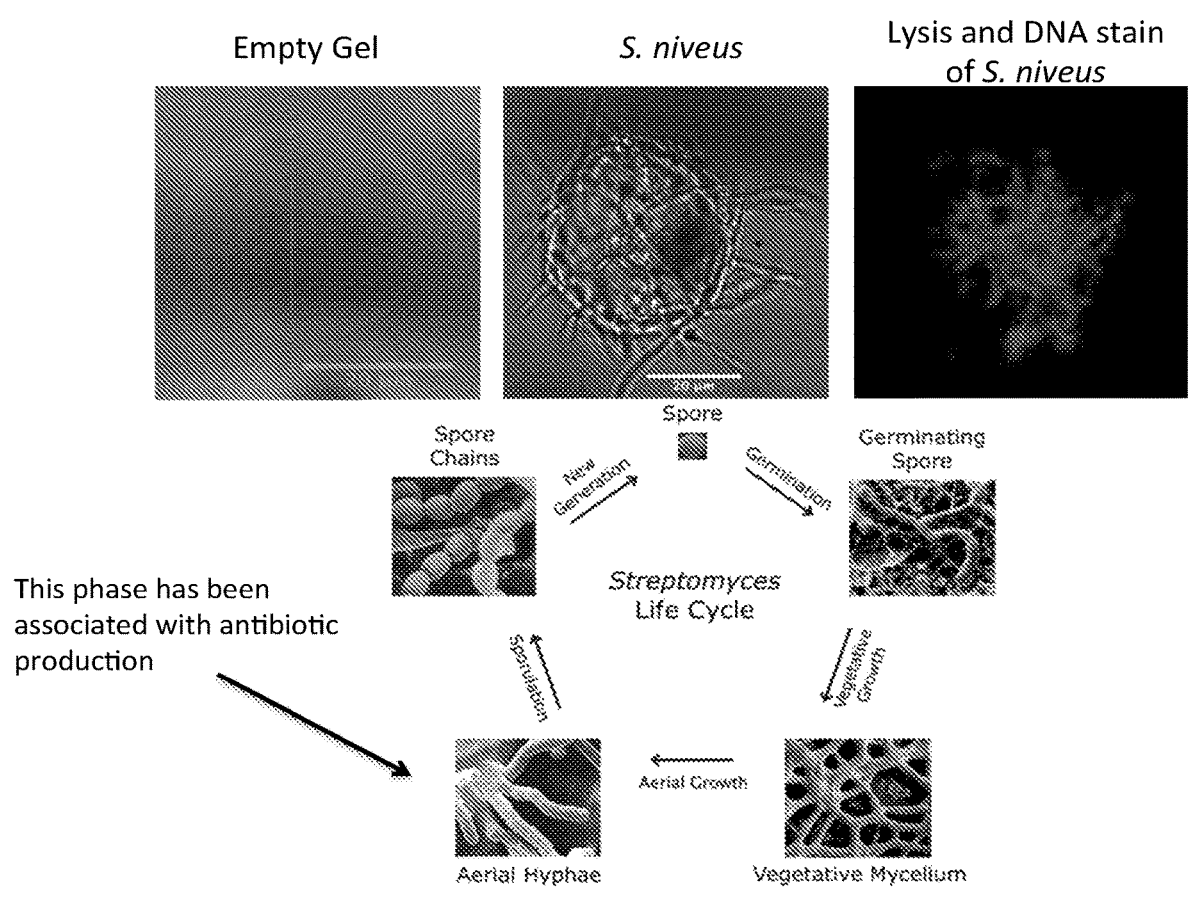
FIG. 6 shows a set of digital images showing *Streptomyces niveus* growth in bead droplets. All images are taken 5 days after encapsulation following phase separation. (Left)

In certain example embodiments, the microscale biological systems encapsulation may be carried out, in whole or in part, on a microfluidic device. FIG. 1 provides an example microfluidic device module that may be used for encapsulation of the microscale biological system in a bead. Other modules capable of merging an aqueous and non-aqueous stream in order to induce droplet formation may also be used. The modules may be configured to obtain loading of a single microscale biological system per bead according to known methods in the art, for example using Poisson loading of droplets. The microscale biological systems flow through a fusion module in a suitable aqueous carrier comprising the first polymer or polymer precursor. The aqueous carrier is then merged with a continuous oil stream which drives formation of individual droplets comprising the first polymer or polymer precursor around a single microscale biological system. Suitable carrier oils include, but are not limited to, known fluorocarbons that are commercially available. The droplets may then be exposed to conditions, either on or off the microfluidic device, which cause the first polymer to polymerize to form a bead around the microscale biological system. As shown in FIG. 2, the process may then be repeated to add an outer capsule to the bead to generate encapsulated beads. The encapsulation process is described in Example 2.

Microfluidic devices disclosed herein may be silicone-based chips and may be fabricated using a variety of techniques, including, but not limited to, hot embossing, molding of elastomers, injection molding, LIGA, soft lithography, silicon fabrication and related thin film processing techniques. Suitable materials for fabricating the microfluidic devices include, but are not limited to, cyclic olefin copolymer (COC), polycarbonate, poly(dimethylsiloxane) (PDMS), and poly(methylacrylate) (PMMA). In one embodiment, soft lithography in PDMS may be used to prepare the microfluidic devices. For example, a mold may be made using photolithography which defines the location of the one or more flow channels and the array of microwells. The substrate material is poured into a mold and allowed to set to create a stamp. The stamp is then sealed to a solid support such as, but not limited to, glass.

Due to the hydrophobic nature of some polymers, such as PDMS, which absorbs some proteins and may inhibit certain biological processes, a passivating agent may be necessary (Schoffner et al. Nucleic Acids Research, 1996, 24:375-379). Suitable passivating agents are known in the art and include, but are not limited to, silanes, parylene, n-Dodecyl-b-D-maltoside (DDM), pluronic, Tween-20, other similar surfactants, polyethylene glycol (PEG), albumin, collagen, and other similar proteins and peptides.

The microfluidic devices may further comprise inlet and outlet ports, or openings, which in turn may be connected to valves, tubes, channels, chambers, and syringes and/or pumps for the introduction and extraction of fluids into and from the microfluidic device. The microfluidic devices may be connected to fluid flow actuators that allow directional movement of fluids within the microfluidic device. Example actuators include, but are not limited to, e.g., syringe pumps, mechanically actuated recirculating pumps, electroosmotic pumps, bulbs, bellows, diaphragms, or bubbles intended to force movement of fluids.

Polymers

The polymers used in the present invention to form the bead and the outer capsule may be the same or different polymers. In certain example embodiments, the polymers are different. In certain example embodiments, the polymer may be a hydrogel polymer. Hydrogel polymers may comprise polysaccharides, synthetic polymers, natural polymer, block copolymers or a combination thereof. Example polysaccharides include hydroxyethyl cellulose, hydroxypropylmethyl cellulose, methyl cellulose, agarose, agar, hydroxyethyl agarose, galactomannan, dextran, or a combination thereof. Example synthetic hydrogels include poly(hydroxyalkyl methacrylates), poly(acrylamide, poly(methacrylamide), poly(N-vinyl-2-pyrrolidone), polyelectrolyte complexes, poly(vinyl alcohol), polyethylene glycol, acylamide matrigel, alginate, functionalized alginate, PAMAM, and derivatives thereof.

In certain example embodiments the first polymer is agarose. In certain other example embodiments, the first and second polymer is agarose. In certain other example embodiments, the first polymer is agarose and the second polymer is polyethylene glycol (PEG).

Microscale Biological Systems

Microscale biological systems that may be screened in the present invention include cell and acellular systems. The cells may be eukaryotic cells, prokaryotic cells, or plant cells. In certain example embodiments, the cells may be naturally occurring. In certain example embodiments, the cells may be isolated from clinical isolates. Any suitably clinical isolate may be used in the present invention including, but are not limited to, a biopsy or other tissue sample, a blood sample, a saliva sample, and a urine sample. In certain example environments the cells may be isolated from an environmental sample. Environmental samples include, but are not limited to household/commercial/industrial surfaces (metal, wood, plastic), soil samples, and water samples (fresh and saline).

In certain example embodiments, the cells may be engineered to comprise one or more genetic perturbations. For example, the sample set could comprise a set of cells, each cell carrying a different genetic perturbation or combination of genetic perturbations to be screened. Genetic perturbations may include gene knock-outs, gene knock-ins, transpositions, inversions, and/or one or more nucleotide insertions, deletions, or substitutions. The set could then be screened using the embodiments disclosed herein to assess an impact the one or more genetic perturbations has on one or more biological functions, to determine a mechanism action, or to identify components of a cell signaling pathway.

In certain example embodiments, the cells are microbial cells. In certain example embodiments, the microbial cells are bacterial cells. In certain other example embodiments, the microbial cells are fungal cells. Any type of microbial cell may be screened using the present assay. For example, the bacterial cells may be screened for production of an antibiotic. In certain example embodiments, the cells are bacterial cells isolated from soil samples. In certain other example embodiments, the cells are bacterial cells isolated from soil samples and screened for antibiotic production. Bacterial genera or species that may be useful in accordance with the invention include, but are not limited to, *Streptomyces, Paenibacillus, Clostridium*. Eukaryotes that may be useful with the invention include, but are not limited to, *Aspergillus, Penicillium, Cephalosporium*, and *Tolypocladium*.

In certain example embodiments, the microscale biological system is an acellular system. An acellular sample may include, but is not limited to, a cellular extract, a cellular fraction or sub-fraction (including nuclear or cytoplasmic fractions or isolated organelles), a cell-free system, and/or an in vitro solution, including but not limited to, an aliquot from an assay screen, probe or experimental solution or reaction. Cell-free systems may comprise a nucleic acid construct or set of nucleic acid constructs encoding a set of gene expression products. Each nucleic acid construct may comprise a different combination of regulatory elements and genes and/or ordering of regulatory elements and genes. Hence, the present invention may be used to screen a set of synthetic biology constructs for one or more target biological functions or to select an optimal construct architecture.

Biological Functions

The embodiments disclosed herein may be used to screen a wide array of biological functions. In certain example embodiments, the microscale biological systems may be screened for a particular type or particular class of biological agent. Example biological agents include expression of certain RNA molecules, production of certain proteins, lipids, polysaccharides, metabolites, small molecules or a combination thereof. In certain other example embodiments, the microscale biological systems may be screened for an ability to impact a biological function of a target cell type. For example, the microscale biological systems may be screened for the ability to induce or inhibit expression of certain expression products in a target cell, to induce phenotypic changes (changes in cell membrane or cell wall morphologies, axonal growth, changes in nuclear or organelle morphologies, changes in cytoskeletal arrangement and/or vesicle trafficking), the ability to induce or inhibit target cell growth, to induce target cell death, the ability to induce neoplastic transformation of a target cell, and/or the ability to induce migration of a target cell.

It should be further understood, the screens for particular biological functions may be done in the further context variable physical parameters, such as different temperatures, atmospheric pressures, pH, growth media conditions, atmospheric $CO_2$ concentrations, atmospheric $O_2$ concentrations, and/or sheer stresses. The microscale biological systems may be exposed to such parameters either before or after encapsulation. Exposure to the above physical parameters may be done on the same microfluidic device used to generate and encapsulate the microscale biological systems, or a separate microfluidic device configured to vary such parameters, or in other discrete volumes outside of a microfluidic device.

In addition, it is possible to alter contents of the capsule or bead to which the microscale biological systems are exposed via diffusion. For example, the contents of the capsule or the bead may be altered by contacting the encapsulated beads with one or more reagents to be diffused into the outer capsule and/or bead. As understood by one of ordinary skill in the art, the type of reagents to be diffused into the outer capsule or bead will further determine the type of polymer that is used in the formation of the outer capsule and bead to ensure the necessary degree of porosity and/or permeability. Example reagents for diffusion into the capsule or bead may include, but are not limited to, reagents necessary to sustain replication or growth of the microscale biological system in the bead, or to sustain replication or growth of a reporter cell (described further below) residing in the outer capsule, reagents to inhibit or induce expression by the microscale biological system, or reagents to detect the presence of target biological agents such as capture agents. Accordingly, the encapsulated beads may be exposed to a carrier comprising the reagent to be diffused into the beads. For example, the encapsulated beads may be maintained in culture medium necessary to sustain growth and expression of the microscale biological system, the make-up of the culture medium being changed or replenished over time. Diffusion of reagents into the encapsulated beads may be done on a microfluidic device or in another suitable discrete volume.

Reporter Elements

As can be appreciated by one of ordinary skill in the art, the biological function to be screened will in part determine the reporter system used. The reporter system may comprise one or more reporter elements that generate a detectable readout. The reporter system may be a reagent or set of reagents that generate a detectable readout upon interaction with a target protein, nucleic acid, metabolite, lipid, polysaccharide, a small molecule, or other indicator of a desired biological function produced by a microscale biological system.

In certain example embodiments, the reporter system produces a detectable signal upon detection of a particular biological function. The detectable signal may be a colorimetric signal, such as a change in color by a pH indicator.

In certain example embodiments, the reporter element may comprise one or more detectable labels. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, ß-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., $^{32}P$, $^{14}C$, $^{125}I$, $^{3}H$, and $^{131}I$), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

In certain example embodiments, the detectable label is a fluorescent label. Examples of fluorescent labels include, but are not limited to, Atto dyes, 4-acetamido-4'-isothiocyanatostilbene-2,2'-disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5-disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoumarin (Coumarin 151); cyanine dyes; cyanosine; 4',6-diamidino-2-phenylindole (DAPI); 5'5''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine.

The fluorescent label may be a fluorescent protein, such as blue fluorescent protein, cyan fluorescent protein, green fluorescent protein, red fluorescent protein, yellow fluorescent protein or any photoconvertible protein. Colorimetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylene. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

In certain other example embodiments, the reporter system may comprise a reporter microscale biological system. A reporter microscale biological system may be a cell or acellular system designed to detect one or more biological functions of the test microscale biological system. For reporter microscale biological systems, the readout may be a phenotypic assessment of the reporter microscale biological system, or detection of one or more reporter elements produced by the reporter microscale biological system. The phenotypic readout may be done using standard cell imaging techniques known in the art. Given the high throughput nature of the method disclosed herein, the cell imaging techniques may comprise high throughput imaging techniques known in the art. Conversely, detection of one or more reporter elements may be done in the same fashion described above for detecting the presence of an indicator of biological function directly from the test microscale biological system itself.

In certain example embodiments, the reporter system detects one or more nucleic acids produced by the test microscale biological systems. Accordingly, the reporter system may comprise one or more reagents that can bind to and produce a detectable signal upon binding to the one or more nucleic acids produced by the test microscale biological system. In certain example embodiments, the reporter system may comprise nucleic acids that hybridize the one or more nucleic acids produced by the microscale biological system. The one or more nucleic acids may be DNA or RNA. In certain example embodiments, the reporter elements bind to one or more mRNAs produced by the microscale biological systems. In certain example embodiments, the nucleic acid reporter elements may undergo a conformational shift upon binding the one or more target nucleic acids that results in emission of a detectable signal. For example, the conformational shift may result in removal of a quencher molecule that otherwise masks the detectable signal until binding to the one or more target nucleic acids. Alternatively, the reporter element may comprise two nucleic acids each labeled with a detectable label that bind to adjacent regions on the one or more target nucleic acids, and wherein binding to the adjacent regions produces emission of a shifted signal from the detectable label, such as that produced through fluorescence resonance energy transfer (FRET).

In certain example embodiments, the reporter system detects a biological molecule produced by the test microscale biological system, including, but not limited to, a protein or peptide, a lipid, a polysaccharide, a metabolite, a small molecule, or any combinations thereof. In some embodiments, a reporter system as described herein may detect more than one such biological molecule as described herein, such as 2, 3, 4, 5, 6, 7, 8, 9, 10, 15, 20, 25, 30, 35, 40, 45, 50, or more biological molecules. The limits of the reporter system of the present invention may be determined by one of skill in the art as appropriate based on the particular application.

In certain example embodiments, the reporter system may comprise a reporter cell. The readout may comprise detecting a change in gene expression, epigenetic modification or chromatin structure of a reporter cell. In certain example embodiments, the readout may comprise detecting phenotypic changes in the reporter cell. Phenotypic changes may include changes in reporter cell morphology, including changes in cell membrane, nuclear, organelle, and/or cytoskeletal morphological changes. Phenotypic changes may also include detecting cell death, neoplastic transformation, or migration of the reporter cell. Phenotypic changes may be assessed using cell imaging techniques known in the art, including high throughput imaging techniques such as those disclosed in Blasi et al. (*Nature Communications* 2016, DOI:10.1038/ncomms10256). Changes in chromatin structure may be detected using nucleic acid proximity detection assays such as Hi-C described in International Patent Application Publication No. WO 2016/089920.

In certain example embodiments the reporter system comprises a reporter cell that is modified so that the readout is expression of a detectable gene expression product. The modification may comprise insertion of a gene expression module into the genome of the reporter cell or insertion of a nucleic acid construct, such as a plasmid, into the reporter cell. In certain example embodiments the gene expression product is operatively connected to a promoter that is inhibited or induced by one or more biological functions of the microscale biological system. In some embodiments, a promoter useful with the invention may be a response promoter. For example, a response promoter may be identified through an RNAseq pathway that is activated upon detection of an extracellular signal or condition that elicits a response in the cell. The signal may convert one or more promoters of genes in a particular pathway. In certain other example embodiments, the promoter may be a stress promoter, such as including, but not limited to, DNA damage response, desiccation response, starvation response, replication checkpoints, cell cycle checkpoints, unfolded protein response, heat/cold, temperature shock response, salt stress, etc. In certain example embodiments, the gene expression product may be a protein. In certain example embodiments, the protein may be a fluorescent protein such as GFP, YFP, RFP, or similar protein. An example reporter cell system is shown in FIG. 7.

In certain example embodiments, the gene expression product may be an mRNA transcript. The mRNA transcript may comprise a defined target sequence recognized by a corresponding probe, wherein the probe is labeled with a detectable label. The reporter cell may comprise different promoters controlling the expression of different mRNA transcript, each separate mRNA transcript comprising a unique sequence recognized by a different probe comprising a different label and thereby able to screen for multiple biological functions at one time.

Sorting and Detecting Biological Agents

In certain example embodiments, the method disclosed herein may further comprise sorting encapsulated beads based at least in part on the detected readout of the one or more reporter elements. As understood by one of ordinary skill in the art, the type of readout will dictate the type of sorting technology that is required. For example, the encapsulated beads may be sorted using flow cytometry, flow imaging cytometry, and flow label-free imaging cytometry. In flow cytometry and flow imaging cytometry, sorting may be based on detection of a detectable label, such as a fluorescent label, of the reporter elements described above. In label-free imaging cytometry, sorting may be done on the basis of differences in size, morphology, or other cellular characteristics and without requiring a detectable label.

In some embodiments, detection may be performed using an antibody pull-down approach. Encapsulated cells can produce proteins that can be captured on the surface of, for example, an agarose bead. These beads can be targeted by magnetic nanoparticle-antibody conjugates (the pore size of an agarose gel is ~200-500 nm). The beads with the corresponding product can then be pulled down by a magnet and further analyzed downstream or in later steps. Such an approach would be similar to an ELISA, but instead of a fluorescent readout with a counter antibody, it may be enriched with a magnet.

In further embodiments, the encapsulated cells can be engineered to produce a compound or enzyme that would degrade or denature the gel. A common choice for this can be matrix metalloproteins, which can break down peptide crosslinks in gels. Any cells that remain embedded within an agarose bead can be discarded through filtration. Cells that manage to break out or proliferate can be separated and followed for further analysis.

Altering Contents of Capsules Via Re-Encapsulation of Beads

In certain example embodiments, the beads may be cycled through a series of re-encapsulations to alter the contents of the outer capsule, to control the types of materials that diffuse into the beads and/or to screen for multiple biological functions within a single assay run. In general, re-encapsulation comprises de-polymerizing the existing outer capsule to release the beads and then re-encapsulating the released beads in a second polymer. The process of re-encapsulation may be carried out as described above. The polymer used in the re-encapsulation process may be the same or different as the capsule used in the initial encapsulation. In certain example embodiments, each re-encapsulation results in the introduction of a new reporter element configured to detect an additional biological function of the microscale biological system. The number of re-encapsulations per assay may be dictated by the number of biological functions to be screened in a single assay. In certain example embodiments, the beads may be exposed to an additional sorting step as described above after each re-encapsulation such that a sub-set of microscale biological systems having the desired combination of biological functions is obtained. In certain other example embodiments, re-encapsulation may be used to introduce additional reagents to sustain replication and/or growth of the biological system or induce or silence expression by the microscale biological system.

Sequencing of Microscale Biological Systems

In certain example embodiments, the methods disclosed herein may further comprise sequencing of the microscale biological systems. Sequencing may comprise DNA sequencing, RNA sequencing, or both. In certain example embodiments, a genotype of the microscale biological systems is determined. In the context of cells, this refers to determining a genotype of the cell in a classical sense. In the context of microscale biological systems comprising a set of nucleic acid constructs determining a "genotype" may refer to sequencing said nucleic acid constructs.

As noted above, the individual discrete volumes comprising the microscale biological systems may be identified using barcodes. In certain example embodiments, the microscale biological system may comprise a unique barcode sequence. In certain example embodiments, the barcode sequence may be a unique naturally occurring sequence that identifies the microscale biological systems, such as a 5S, 16S, or 23S rRNA sequence. Alternatively, in some example embodiments, the microscale biological system may be modified to include a barcode sequence. For example, a unique barcode sequence may be inserted into the genomic sequence of a cellular microscale biological system or into a nucleic acid construct of an acellular or synthetic system. Nucleic acid barcodes may be used to de-convolute sequencing data and correlate nucleic acid sequences with individual discrete volumes from which the sequence information was obtained.

In certain example embodiments, determining a genotype of the microscale biological system may comprise lysing the cell in each bead such that genomic DNA is retained in the gel beads. As one of the ordinary skill in the art will appreciate, the lysing step is not required in cell free systems. The beads are then released from the first outer capsule and re-encapsulated in a second outer capsule comprising genomic DNA amplification reagents. The beads are then maintained under conditions sufficient for genomic DNA amplification. After genomic DNA amplification, the beads are released from the second outer capsule and re-encapsulated in a third outer capsule comprising tagmentation reagents. In certain example embodiments, the tagmentation reagents are delivered such that each droplet receives a transposome complex comprising a unique origin-specific barcode or unique combination of origin specific barcodes. The beads are then maintained under conditions sufficient for tagmentation resulting in genomic DNA fragment labeled with sequencing adapters, and optionally, origin-specific barcodes. The genomic DNA fragments are then isolated and used to prepare a DNA sequencing library. The genotype of each microscale biological system may then be determined by sequencing the DNA sequencing library.

In certain example embodiments, sequencing may comprise determining the sequence of some or all of the RNA transcripts expressed by a microscale biological system. RNA sequencing may be done using known RNA sequencing methods in the art. In certain example embodiments, transcriptome sequencing is done using a method such as drop-seq as disclosed in Macosko et al. "Highly Parallel Genome-wide Expression Profiling of Individual Cells Using Nanoliter Droplets." Cell, 2015, 161:1202-1214 and Klein et al. "Droplet Barcoding for Single-Cell Transcriptomics Applied to Embryonic Stem Cells" Cell, 2015, 161: 1187-1201.

EXAMPLE EMBODIMENTS

In one example embodiment, the embodiments disclosed herein are used to screen bacterial cells for biological functions. In certain example embodiments, the biological function is production of one or more bacterial cell products exhibiting antibiotic activity. In certain example embodiments, the bacteria may comprise different species of bacteria, different strains of the same species of bacteria, or a combination thereof. The bacteria may be isolated from a natural environment. For example, many existing antibiotics are produced by bacterial species commonly found in the soil. Therefore, one example application would be the screening of bacteria obtained from soil samples for novel antibiotic activity.

The bacteria to be screened are encapsulated in a first polymer. In certain example embodiments, the first polymer is agarose. In certain example embodiments, the cells to be screened are loaded into a microfluidic device in combination with molten agarose, wherein the microfluidic device induces droplet formation from the molten agarose by flowing a stream of carrier oil into a stream comprising the molten agarose and bacteria cells to be screened. The flow rate of the molten agarose and carrier oil streams may be controlled using known methods in the art to result in Poisson loading of individual cells into individual agarose droplets.

The agarose droplets are then cooled and allowed to polymerize. This may be achieved by flowing the newly formed droplet through an incubation channel or series of incubation channels that exposed the agarose droplets to reduced temperatures and thereby allow the agarose to cool and polymerize. The result is a library of beads encapsulating individual bacteria i.e. "producer cells" or "producer strains."

The beads are then again encapsulated in an outer capsule (i.e. second individual discrete volume) by substantially repeating the process used to generate the beads. However, in addition to adding the beads to a solution comprising a second polymer, the solution further comprises a second bacterium, or reporter strain. This reporter stain may be a single species or combination of species. In certain example embodiments, the reporter strain is a representative species of a bacterium to which effective antibiotics are desired. The outer capsule is formed the same way as the initial bead. Where the second polymer is agarose it will be understood that the initial agarose bead will depolymerize and repolymerize with the outer capsule such that the initial discrete volume formed by the first bead may become continuous with the larger agarose droplet upon re-polymerization. However, where a second polymer is used that polymerizes under different conditions, the initial bead may remain distinct with the larger final droplet. The second polymer should allow diffusion of products generated by the produced strain in the bead to diffuse out into the outer capsule in order to contact the reporter strain.

Once formed, the system may be incubated to allow for growth of the reporter and producer strains. Antibiotic activity may be assessed by observation of growth characteristics of the reporter strain. For example, the reporter strain may be assigned for signs of cell death, inhibited growth relative to controls, or for zones of inhibition around the producer strain or inner bead. In certain example embodiments, the reporter strain may further comprise a reporter element. In certain example embodiments the reporter element is a nucleic acid construct introduced into the report strain, the nucleic acid construct comprising a fluorescent protein operably connected to a stress reporter. As shown in FIG. 7, in an unstressed cell the stress promoter is normally repressed. Repression is removed upon exposure of the reporter strain to stresses such as exposure to bactericidal antibiotics. Accordingly, expression of the fluorescent protein is induced when the reporter strain is exposed to an antibiotic from the producer strain and this fluorescent signal may then be detected using the imaging and/or cell sorting modalities described above. For example, FACS may be used to sort producer strains exhibiting antibiotic activities from those that do not. In this way the reporter strains and/or products produced by the reporter may then be further isolated and characterized.

The invention is further described in the following examples, which do not limit the scope of the invention described in the claims.

EXAMPLES

Example 1

In one example embodiment, determining a genotype of the microscale biological system comprises encapsulation of single cells into a first droplet. In certain example embodiments, the polymer used to form the first droplet is agarose. The agarose is maintained at a molten temperature during droplet formation. After encapsulation in droplets the droplets are cooled, allowing the agarose to polymerize. The cells are then lysed with the agarose bead, for example, by exposure of the beads to alkaline conditions or other cell lysis conditions known in the art and suitable for lysing a cell within the agarose bead. The beads containing lysed cells are then encapsulated in a second polymer. In certain example embodiments, the second polymer is PEG. The beads may be encapsulated in a polymer comprising PEG precursors and multiple displacement amplification (MDA) reagents. The PEG precursors are polymerized to form the outer capsule. The MDA reaction may be carried out under conditions and for a time known in the art to be sufficient for the MDA reaction. After the MDA reaction, the beads are released from the outer capsule. In certain example embodiments, the emulsions may be broken using perfluorooctanol. At this point, the amount of genomic DNA per gel bead can be quantified using qPCR. In order to prepare for sequencing, the individual beads are then re-encapsulated with a tagmentation mix. After the tagmentation reaction, the encapsulated beads are Poisson loaded into an additional individual discrete volume, such as the wells of a 96-well plate, containing library amplification reagents. The amplified, fragmented, and transposon-labeled DNA is then released from the bead and capsule, for example using electrocoalescence, then subjected to library amplification in the individual discrete volume.

FIG. 15 provides an overview of an example process. FIG. 16 shows the results of an experiment monitoring MDA reactions in droplets loaded with either 0.1 molecules of DNA, single cells, or nothing. DNA/cells were loaded into an agarose bead, lysed with alkaline solution, and the beads were reemulsified into an MDA master mix. The reaction was allowed to proceed for sixteen hours. After reaction, the gels were placed into the aqueous phase with perfluorooctanol where reagent exchange and further washing took place. FIG. 17 shows quantification of yields from MDA positive or no template control "NTC." Each color is a unique gene in the *E. coli* genome and data for four genes is shown per sample. Beads were quantified on a hemocytometer and then diluted to approximately 10 *E. coli* containing beads per reaction. A Taqman qPCR assay was carried out on each of the genes using *E. coli* genomic DNA as a standard. The absence of a data point means that the product was not detectable through this assay. FIG. 18 is an example of a tagmented library generated through emulsion tagmentation. The x-axis is bp size and the y-axis is intensity. The size of this library is in the typical 300-800 base pair range. Tagmentation was carried out with a 1× Nextera enzyme in tris acetate, $MgCl_2$ buffer. Tagmented beads were placed directly into a PCR reaction with no wash step in between. The transposase was removed through heat denaturation at 72° C.

FIG. 19 shows sequencing coverage of the E. coli genome from five different gel beads. X-axis shows genome position and the y-axis shows reads per location. Each color represents a different sample of E. coli. The spikey nature of the reads is typical for MDA bias.

Example 2—Encapsulation of Cells

First Encapsulation
1) Heat a 2% agarose gel solution at 75° C. for 10 min. Also place device on a hot plate set to 37° C.
2) Cool down to 37° C. for 5 min.
3) Filter Biorad droplet generation oil through 0.22 lam filter.
4) Load two syringe pumps with the corresponding solutions (oil and aqueous). Set the oil solution at 600 μL/hr and the aqueous solution at 150 μL/hr.
5) Coat device channels with aquapel for 20 sec and air dry.
6) Generate droplets for 20 min to 1 hr, depending on how many are required.
7) Cool gel beads to 4° C. for 1 hr to gel beads.
8) Electrocoalesce the beads into a new aqueous solution and concentrate through centrifugation.

Second encapsulation
1) Prep new microfluidic device in the same fashion as described above.
2) Load a third syringe pump with the agarose bead slurry. Inject at 25 μL/hr into device designed for reencapsulation (with oil (600 μl/hr) and new aqueous solution (100 μL/hr)).
3) Generate droplets for as long as required.

Example 3—Alternative Methods for Encapsulation

TABLE 1

Acrylamide mix (non-degradable)

| Component | Amount(ul) |
|---|---|
| Nuclease-free water | 620 |
| 1 × TBSET buffer | 100 |
| 4 × Acrylamide/Bisacrylamide solution | 250 |
| 10% (wt/vol) APS- make fresh | 30 |
| Total | 1000 |

TABLE 2

Acrylamide mix (degradable, the degradable part being DHEBA)

| Component | Amount(ul) |
|---|---|
| Nuclease-free water | 620 |
| 1 × TBSET buffer | 100 |
| 2 × Acrylamide/Bisacrylamide/DHEBA solution* | 250 |
| 10% (wt/vol) APS- make fresh | 30 |
| Total | 1000 |

*2× Acrylamide/Bisacrylamide/DHEBA solution is 10% acrylamide/bisacrylamide and 0.5% DHEBA First Encapsulation)
1) Make up acryladmide mastermix as shown above.
2) Mix TEMED and carrier oil (4 μL TEMED into 1 mL droplet generation oil).
3) Filter Biorad droplet generation oil through 0.22 lam filter.
4) Load two syringe pumps with the corresponding solutions (oil and aqueous). Set the oil solution at 500 μL/hr and the aqueous solution at 150 μL/hr.
5) Coat device channels with aquapel for 20 sec and air dry.
6) Generate droplets for 20 min to 1 hr, depending on how many are required.
7) Overlay with mineral oil and polymerize at 60 C overnight.
8) Electrocoalesce the beads into a new aqueous solution, wash, and concentrate through centrifugation.

Second Encapusulation (Two Approaches)
Approach 1 (Droplet Microfluidics))
1) Prep new microfluidic device in the same fashion as described above.
2) Load a third syringe pump with the agarose bead slurry. Inject at 25 μL/hr into device designed for reencapsulation (with oil (600 μl/hr) and new aqueous solution (100 μL/hr)).
3) Generate droplets for as long as required.

Approach 2 (Vortex)
1) Mix oil and second encapsulation gel mix at a ratio of 4:1.
2) Vortex at max setting for 30 secs.
3) Overlay with mineral oil and polymerize at 60 C overnight.
4) Electrocoalesce the beads into a new aqueous solution, wash, and concentrate through centrifugation.

Example 4—Creating a Cavity within a Gel (can be Done Before or after MDA)

MDA (Same Protocol as Before)
MDA was performed according to manufacturer's protocol (Qiagen Repli G single cell kit).
1) Make an MDA mastermix according to the above.
2) generate a liquid emulsion around gel beads by vortexing the mixtures of beads and MDA mastermix.
3) incubate at 30 C for 16 hrs.

Loading TN5 with Fluorescent Adapters
Protocol adapted from Amini, S. et al Haplotype-resolved whole-genome sequencing by contiguity-preserving transposition and combinatorial indexing. Nat. Gen. 46, 1343-1349 (2014).

Transposases were expressed, purified, and assembled following methods published previously. DNA containing unique fluorescent tag and the 19 bp mosaic end were annealed by incubating 100 uM of DNA from 95 C to 25 C at 0.1 C/sec and holding at 88, 74, 60, and 37 C for 2 min each. The annealed oligos and transposases were mixed at 12.5 uM and incubated at 37 C for 1 hour before storing at −20 C.

Loading TN5 with Barcode Adapters (Same as Above, but Loaded with Different DNA Adapters)
Transposases was expressed, purified, and assembled followed methods published previously. DNA containing barcodes, read 1 sequencing primer, read 2 sequencing primer, and the 19 bp mosaic end were annealed by incubating 100 uM of DNA from 95 C to 25 C at 0.1 C/sec and holding at 88, 74, 60, and 37 C for 2 min each. The annealed oligos and transposases were mixed at 12.5 uM and incubated at 37 C for 1 hour before storing at −20 C.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method for screening biological functions of microscale biological systems, comprising:
    segregating each microscale biological system from a set of microscale biological systems into a first individual discrete volume, the first individual discrete volume comprising a first polymer;
    polymerizing the first polymer to form a set of polymerized gel beads, wherein each gel bead encapsulates an individual microscale biological system;
    encapsulating each gel bead in a second individual discrete volume, the second individual discrete volume comprising a second polymer and one or more reporter elements capable of producing a readout indicating an absence or presence of one or more chemical or biological agents produced by the individual microscale biological system and indicating one or more target biological functions of the individual microscale biological system, wherein the first and second polymers are different;
    polymerizing the second polymer to form an individual outer capsule around each gel bead comprising the one or more reporter elements thereby generating a set of encapsulated gel beads, wherein each encapsulated gel bead double encapsulates an individual microscale biological system;
    forming the readout within the outer capsule upon diffusion of the one or more chemical or biological agents out of the gel bead and into the outer capsule, such that the individual microscale biological system is retained in the gel bead and the one or more reporter elements are retained in the outer capsule; and
    identifying the one or more target biological functions of each microscale biological system based at least in part on detecting the readout formed within the outer capsule by the one or more reporter elements, after which each gel bead is capable of being released from the outer capsule comprising the one or more chemical or biological agents, the one or more reporter elements, and the formed readout, and capable of being re-encapsulated by an additional outer capsule.

2. The method of claim 1, further comprising:
    sorting the identified encapsulated gel beads based at least in part on the detected readout of the one or more reporter elements;
    isolating the sorted encapsulated gel beads identified as having the one or more target biological functions;
    analyzing the isolated encapsulated gel beads for the one or more chemical or biological agents produced by the microscale biological systems; and
    sequencing the microscale biological systems of the analyzed encapsulated gel beads.

3. The method of claim 2, wherein the one or more chemical or biological agents are an expressed RNA, a protein, a lipid, a polysaccharide, a small molecule, a metabolite, or a combination thereof; and/or
    wherein one or more capture agents for the one or more chemical or biological agents are introduced into the gel bead, outer capsule, or both and the method further comprises isolating the one or more capture agents.

4. The method of claim 2, wherein the microscale biological systems are cells, and wherein the microscale biological systems sequencing step comprises determining a genotype for each cell.

5. The method of claim 4, wherein the determining the genotype for each cell step comprises:
    lysing the cell in each gel bead such that genomic DNA is retained in the gel bead;
    releasing the gel beads from the first outer capsule;
    re-encapsulating the gel beads in a second outer capsule, the second outer capsule comprising genomic DNA amplification reagents;
    maintaining the encapsulated gel beads under conditions sufficient for genomic DNA amplification;
    releasing the gel beads from the second outer capsule;
    re-encapsulating the gel beads in a third outer capsule, the third outer capsule comprising tagmentation reagents to generate genomic DNA fragments, wherein tagmentation reagents are delivered such that each encapsulated gel bead receives transposome complexes comprising a unique origin-specific barcode or unique combination of origin-specific barcodes;
    maintaining the encapsulated gel beads under conditions sufficient for tagmentation such that the genomic DNA fragments are labeled with sequencing adapters and origin-specific barcodes;
    isolating the tagmented DNA fragments from the gel beads to obtain a DNA sequencing library comprising genomic DNA fragments;
    sequencing the DNA sequencing library; and
    determining the genotype of each cell by assembly of sequence DNA reads based on common origin-specific barcodes.

6. The method of claim 5, wherein the DNA amplification reagents are multiple displacement amplification (MDA) reagents.

7. The method of claim 5, further comprising a DNA sequencing library amplification step prior to the DNA sequencing library sequencing step, wherein, optionally, the DNA sequencing library amplification step comprises:
    releasing each encapsulated gel bead into a separate individual discrete volume comprising DNA amplification reagents;
    breaking the encapsulated gel bead to release genomic DNA fragments labeled with sequencing adapters and origin specific barcodes into the individual discrete volume; and
    maintaining the individual discrete volumes under conditions sufficient to allow for DNA amplification.

8. The method of claim 7, wherein the DNA sequencing library amplification step comprises addition of a second barcode to each genomic DNA fragment.

9. The method of claim 1, further comprising altering the contents of the identified encapsulated gel beads, wherein altering the contents of the identified encapsulated gel beads comprises releasing the gel beads from the first outer capsule and re-encapsulating the gel beads in an additional outer capsule, wherein the additional outer capsule comprises reagents to sustain replication or growth of the microscale biological system, silence or induce expression by the microscale biological system, or determine an additional biological function of the microscale biological system.

10. The method of claim 9, wherein the steps of releasing and re-encapsulating the gel beads are repeated over a number of biological functions to be tested, wherein each re-encapsulation introduces a new set of reagents and/or reporter elements for determining a given biological function, and wherein, after each round of releasing and re-encapsulating the gel beads, the method further comprises:
   forming a readout produced by the new set of reporter elements within the additional outer capsule upon diffusion of one or more chemical or biological agents out of the gel bead and into the additional outer capsule, during which the microscale biological system is retained in the gel bead and the new set of reporter elements are retained in the additional outer capsule; and
   identifying the additional target biological function of each microscale biological system based at least in part on detecting the readout formed within the additional outer capsule by the new set of reporter elements.

11. The method of claim 10, further comprising, after identifying the one or more target biological functions and after each round of identifying the additional target biological function:
   sorting the identified encapsulated gel beads based at least in part on the detected readout produced by the one or more reporter elements in the first outer capsule or the new set of reporter elements in the additional outer capsule.

12. The method of claim 1, wherein the reporter element is a reporter cell, and wherein the readout comprises cell growth, cell death, changes in reporter cell gene expression, changes in reporter cell epigenetic modifications or chromatin structure, or phenotypic changes.

13. The method of claim 12, wherein the reporter cell is modified so that the readout is expression of a detectable gene expression product, optionally,
   wherein the detectable gene expression product is operatively connected to a promoter that is inhibited or induced by one or more biological functions of the microscale biological systems, optionally, wherein the promoter is a stress promoter; and/or
   wherein the detectable gene expression product is a fluorescent protein.

14. The method of claim 1, wherein the set of microscale biological systems comprises naturally occurring cells, optionally,
   wherein the naturally occurring cells are prokaryotic cells, eukaryotic cells, or a mixture thereof; or
   wherein the naturally occurring cells are derived from clinical isolates; or
   wherein the naturally occurring cells are derived from one or more environmental samples; or
   wherein the naturally occurring cells are prokaryotic cells to be screened for antibiotic production.

15. The method of claim 1, wherein the set of microscale biological systems comprises engineered cells comprising one or more genetic perturbations.

16. The method of claim 1, wherein the set of microscale biological systems comprises a set of cell free systems, optionally, wherein each cell free system comprises one or more nucleic acid constructs comprising one or more modules encoding a gene expression product and one or more gene expression regulator elements, optionally, wherein each cell free system comprises a different combination and/or ordering of gene expression modules and gene expression regulator elements.

17. The method of claim 9, wherein the polymer used to form the first outer capsule and the polymer used to form the additional outer capsule are the same or different.

18. The method of claim 1, wherein the first polymer, second polymer, or both are a hydrogel polymer.

19. The method of claim 18, wherein the hydrogel polymer comprises a polysaccharide, a synthetic polymer, a natural polymer, and/or a block copolymer, optionally, wherein the polysaccharide comprises hydroxyethyl cellulose, hydroxypropylmethyl cellulose, methyl cellulose, agarose, agar, hydroxyethyl agarose, galactomannan, dextran or a combination thereof.

20. The method of claim 1, wherein the reporter element produces an optically detectable readout.

21. The method of claim 1, wherein the reporter element comprises magnetic-based separation, wherein, optionally, the magnetic-based separation comprises labeling a biological molecule of interest with a magnetic particle and isolating the biological molecule of interest using the magnetic particles, and wherein, optionally, the biological molecule of interest is selected from the group consisting of a protein, a cell surface marker, a nucleic acid, and combinations thereof.

22. The method of claim 1, further comprising altering the contents of the identified encapsulated gel beads, wherein altering the contents of the identified encapsulated gel beads comprises contacting the identified encapsulated gel beads with one or more reagents that are diffusible into the outer capsule and/or gel bead, wherein the one or more reagents are used to sustain replication or growth of the microscale biological system in the gel bead, silence or induce expression by the microscale biological system, or determine an additional biological function of the microscale biological system.

23. The method of claim 2, wherein the microscale biological systems sequencing step comprises labeling each sequence of each microscale biological system in an individual gel bead with an origin-specific barcode.

24. The method of claim 2, wherein the microscale biological system is a cell, and wherein the microscale biological systems sequencing step comprises determining a transcriptome of all expressed RNA sequences.

25. The method of claim 2, wherein the microscale biological system is a cell free system comprising one or more nucleic acid constructs, and wherein the microscale biological systems sequencing step comprises determining a sequence of the one or more nucleic acid constructs.

26. The method of claim 25, wherein the determining a sequence of the one or more nucleic acid constructs step comprises:
   releasing the gel beads from the first outer capsule;
   re-encapsulating the gel beads in a second outer capsule, the second outer capsule comprising genomic DNA amplification reagents;
   maintaining the encapsulated gel beads under conditions sufficient for genomic DNA amplification;
   releasing the gel beads from the second outer capsule;

re-encapsulating the gel beads in a third outer capsule, the third outer capsule comprising tagmentation reagents to generate genomic DNA fragments, wherein tagmentation reagents are delivered such that each encapsulated gel bead receives transposome complexes comprising a unique origin-specific barcode or unique combination of origin-specific barcodes;

maintaining the encapsulated gel beads under conditions sufficient for tagmentation such that the genomic DNA fragments are labeled with sequencing adapters and origin-specific barcodes;

isolating the tagmented DNA fragments from the gel beads to obtain a DNA sequencing library comprising genomic DNA fragments;

sequencing the DNA sequencing library; and determining the genotype of the one or more nucleic constructs of each gel bead by assembly of sequence DNA reads based on common origin-specific barcodes.

27. The method of claim 26, wherein the DNA amplification reagents are multiple displacement amplification (MDA) reagents.

28. The method of claim 27, further comprising a DNA sequencing library amplification step prior to the DNA sequencing library sequencing step, wherein, optionally, the DNA sequencing library amplification step comprises:

releasing each encapsulated gel bead into a separate individual discrete volume comprising DNA amplification reagents;

breaking the encapsulated gel bead to release genomic DNA fragments labeled with sequencing adapters and origin specific barcodes into the individual discrete volume; and maintaining the individual discrete volumes under conditions sufficient to allow for DNA amplification.

29. The method of claim 28, wherein the DNA sequencing library amplification step comprises addition of a second barcode to each genomic DNA fragment.

30. The method of claim 1, wherein, prior to and/or during the polymerizing the first polymer to form a set of polymerized gel beads, the method excludes contacting the microscale biological systems with one or more expression reagents and/or one or more amplification reagents.

* * * * *